(12) United States Patent
Soo et al.

(10) Patent No.: US 12,144,843 B2
(45) Date of Patent: Nov. 19, 2024

(54) METHODS AND COMPOSITIONS FOR MODULATING MYOFIBROBLAST ACTIVITIES

(71) Applicant: THE REGENTS OF THE UNIVERSITY OF CALIFORNIA, Oakland, CA (US)

(72) Inventors: B. Chia Soo, Los Angeles, CA (US); Kang Ting, Los Angeles, CA (US); Zhong Zheng, Van Nuys, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/928,724

(22) Filed: Jul. 14, 2020

(65) Prior Publication Data

US 2020/0345811 A1    Nov. 5, 2020

Related U.S. Application Data

(60) Continuation-in-part of application No. 16/405,782, filed on May 7, 2019, now Pat. No. 10,729,747, which is a continuation of application No. 15/673,880, filed on Aug. 10, 2017, now Pat. No. 10,279,010, which is a division of application No. 14/106,617, filed on Dec. 13, 2013, now Pat. No. 9,744,214, which is a continuation of application No. PCT/US2012/042517, filed on Jun. 14, 2012.

(60) Provisional application No. 61/497,397, filed on Jun. 15, 2011.

(51) Int. Cl.
  *A61K 38/18* (2006.01)
  *A61K 38/17* (2006.01)

(52) U.S. Cl.
  CPC .......... *A61K 38/1841* (2013.01); *A61K 38/17* (2013.01); *A61K 38/1709* (2013.01)

(58) Field of Classification Search
  CPC .............. C07K 14/7051; C07K 1/1077; C07K 14/505; C07K 14/705; C07K 2319/30; C07K 14/755; C07K 1/20; C07K 1/34; C07K 2319/02; C07K 2319/03; C07K 2319/33; C07K 2319/50; C07K 14/435; C07K 14/43518; C07K 14/43522; C07K 14/4726; C07K 14/70521; C07K 16/22; C07K 16/244; C07K 16/248; C07K 16/2875; C07K 16/2887; C07K 16/42; C07K 2317/21; C07K 2319/21; C07K 2319/43; C07K 14/001; C07K 14/195; C07K 14/47; C07K 14/70539; C07K 14/70564; C07K 14/70578; C07K 14/70589; C07K 14/78; C07K 14/8125; C07K 16/2878; C07K 17/00; C07K 19/00; C07K 2318/20; C07K 2319/01; C07K 2319/70; C07K 14/4725; C07K 7/08; C07K 9/00; C07K 14/4713; A61P 27/02; A61P 9/00; A61P 1/00; A61P 25/00; A61P 1/16; A61P 11/00; A61P 13/00; A61P 13/12; A61P 19/00; A61P 21/00; A61P 21/06; A61P 7/00; A61P 17/02; A61P 29/00; A61P 43/00; A61P 11/06; A61P 17/00; A61P 3/10; A61K 38/39; A61K 47/61; A61K 9/146; A61K 48/005; A61K 2039/545; A61K 2239/31; A61K 2239/38; A61K 2239/57; A61K 39/395; A61K 39/4611; A61K 47/549; A61K 47/64; A61K 47/6425; A61K 47/6937; A61K 2039/505; A61K 2039/54; A61K 2039/55; A61K 2039/55561; A61K 2039/585; A61K 2300/00; A61K 31/337; A61K 31/728; A61K 35/12; A61K 35/22; A61K 35/28; A61K 35/34; A61K 35/36; A61K 38/00; A61K 38/177; A61K 39/0011; A61K 39/001104; A61K 39/001106; A61K 39/001129; A61K 39/39; A61K 39/4631; A61K 39/4632; A61K 39/4636; A61K 39/464464; A61K 39/464488; A61K 39/464492; A61K 39/464499; A61K 39/464838; A61K 47/42; A61K 47/544; A61K 47/55; A61K 47/60; A61K 47/6415; A61K 47/65; A61K 47/68; A61K 48/00; A61K 49/0032; A61K 49/0034; A61K 49/0056; A61K 49/0058; A61K 51/08

See application file for complete search history.

(56) References Cited

U.S. PATENT DOCUMENTS

| | | |
|---|---|---|
| 9,744,214 B2 | 8/2017 | Soo et al. |
| 10,279,010 B2 | 5/2019 | Soo et al. |
| 10,729,747 B2 | 8/2020 | Soo et al. |
| 2008/0152639 A1 | 6/2008 | Soo |
| 2009/0082856 A1 | 3/2009 | Flanagan |
| 2011/0086807 A1 | 4/2011 | Soo |

(Continued)

FOREIGN PATENT DOCUMENTS

| | | | |
|---|---|---|---|
| WO | WO2010/138637 A2 * | 12/2010 | ........... C07K 14/435 |
| WO | 2012174280 A2 | 12/2012 | |

OTHER PUBLICATIONS

Soo, B. Chia; Non-Final Office Action for U.S. Appl. No. 16/405,782, filed May 7, 2019, mailed Nov. 4, 2019; 14 pages.

(Continued)

*Primary Examiner* — Audrea B Coniglio
(74) *Attorney, Agent, or Firm* — Taylor English Duma LLP

(57) ABSTRACT

The present invention discloses methods and compositions for treating or ameliorating a condition associated with increased or decreased myofibroblast activities and use thereof.

14 Claims, 6 Drawing Sheets

Specification includes a Sequence Listing.

(56) References Cited

U.S. PATENT DOCUMENTS

| | | | |
|---|---|---|---|
| 2013/0251758 A1* | 9/2013 | Everland | A61L 27/18 424/400 |
| 2014/0105939 A1 | 4/2014 | Soo et al. | |
| 2017/0333528 A1 | 11/2017 | Soo et al. | |
| 2019/0321445 A1 | 10/2019 | Soo et al. | |

OTHER PUBLICATIONS

Soo, Chia B; Advisory Action for U.S. Appl. No. 14/106,617, filed Dec. 13, 2013, mailed Sep. 20, 2016, 03 pgs.
Soo, Chia B; Applicant Initiated Interview Summary for U.S. Appl. No. 14/106,617, filed Dec. 13, 2013, mailed Jan. 22, 2016, 03 pgs.
Soo, Chia B; Final Office Action for U.S. Appl. No. 14/106,617, filed Dec. 13, 2013, mailed May 23, 2016, 09 pgs.
Soo, Chia B; Issue Notification for U.S. Appl. No. 14/106,617, filed Dec. 13, 2013, mailed Aug. 9, 2017, 01 pg.
Soo, Chia B; Non-Final Office Action for U.S. Appl. No. 14/106,617, filed Dec. 13, 2013, mailed Oct. 20, 2016, 09 pgs.
Soo, Chia B; Non-Final Office Action for U.S. Appl. No. 14/106,617, filed Dec. 13, 2013, mailed Oct. 22, 2015, 09 pgs.
Soo, Chia B; Notice of Allowance for U.S. Appl. No. 14/106,617, filed Dec. 13, 2013, mailed Apr. 26, 2017, 08 pgs.
Soo, Chia B; Requirement for Restriction/Election for U.S. Appl. No. 14/106,617, filed Dec. 13, 2013, mailed May 12, 2015, 09 pgs.
Soo, Chia B ; Non-Final Office Action for U.S. Appl. No. 15/673,880, filed Aug. 10, 2017, mailed Sep. 13, 2018, 10 pgs.
Soo, Chia B ; Non-Final Office Action for U.S. Appl. No. 15/673,880, filed Aug. 10, 2017, mailed Mar. 27, 2018, 10 pgs.
Soo, Chia B.; Issue Notification for U.S. Appl. No. 15/673,880, filed Aug. 10, 2017, mailed Apr. 17, 2019, 01 pg.
Soo, Chia B.; Requirement for Restriction/Election for U.S. Appl. No. 15/673,880, filed Aug. 10, 2017, mailed Jan. 2, 2018, 06 pgs.
Soo, Chia B; Advisory Office Action for U.S. Appl. No. 15/673,880, filed Aug. 10, 2017, mailed Nov. 14, 2018, 03 pgs.
Soo, Chia B; Final Office Action for U.S. Appl. No. 15/673,880, filed Aug. 10, 2017, mailed Sep. 13, 2018, 10 pgs.
Soo, Chia B; Notice of Allowance for U.S. Appl. No. 15/673,880, filed Aug. 10, 2017, mailed Feb. 6, 2019, 10 pgs.
Soo, B. Chia; Issue Notification for U.S. Appl. No. 16/405,782, filed Aug. 4, 2020, mailed Jul. 15, 2020; 1 page.
Soo, B. Chia; Notice of Allowance for U.S. Appl. No. 16/405,782, filed May 7, 2019; mailed Mar. 25, 2020; 7 pages.
Soo, Chia B.; International Preliminary Report on Patentability for serial No. PCT/US2012/042517, filed on Jun. 14, 2012, mailed Jan. 3, 2014, 5 pgs.
Soo, Chia B .; International Search Report and Written Opinion for serial No. PCT/US2012/042517, filed on Jun. 14, 2012, mailed Feb. 1, 2013, 8 pgs.
Andriamanalijaona, R. et al. "Effect of Interleukin-1 beta on Transforming Growth Factor-Beta and Bone Morphobenic Protein-2 Expression in Human Periodontal Ligament and Alveolar Bone Cells in Culture: Modulation by Avocado and Soybean Unsaponifiables", 11 pgs.

* cited by examiner

SEQUENCE LISTING

```
<160> NUMBER OF SEQ ID NOS: 66

<210> SEQ ID NO 1
<211> LENGTH: 374
<212> TYPE: PRT
<213> ORGANISM: Homo sapiens

<400> SEQUENCE: 1

Trp Thr Ser Leu Leu Leu Ala Gly Leu Phe Ser Leu Ser Gln Ala
1               5                   10                  15

Gln Tyr Glu Asp Asp Pro His Trp Trp Phe His Tyr Leu Arg Ser Gln
                20                  25                  30

Gln Ser Thr Tyr Tyr Asp Pro Tyr Asp Pro Tyr Pro Tyr Glu Thr Tyr
            35                  40                  45

Glu Pro Tyr Pro Tyr Gly Val Asp Glu Gly Pro Ala Tyr Thr Tyr Gly
        50                  55                  60

Ser Pro Ser Pro Pro Asp Pro Arg Asp Cys Pro Gln Glu Cys Asp Cys
65                  70                  75                  80

Pro Pro Asn Phe Pro Thr Ala Met Tyr Cys Asp Asn Arg Asn Leu Lys
                85                  90                  95

Tyr Leu Pro Phe Val Pro Ser Arg Met Lys Tyr Val Tyr Phe Gln Asn
            100                 105                 110

Asn Gln Ile Thr Ser Ile Gln Glu Gly Val Phe Asp Asn Ala Thr Gly
        115                 120                 125

Leu Leu Trp Ile Ala Leu His Gly Asn Gln Ile Thr Ser Asp Lys Val
    130                 135                 140

Gly Arg Lys Val Phe Ser Lys Leu Arg His Leu Glu Arg Leu Tyr Leu
145                 150                 155                 160

Asp His Asn Asn Leu Thr Arg Met Pro Gly Pro Leu Pro Arg Ser Leu
                165                 170                 175

Arg Glu Leu His Leu Asp His Asn Gln Ile Ser Arg Val Pro Asn Asn
            180                 185                 190

Ala Leu Glu Gly Leu Glu Asn Leu Thr Ala Leu Tyr Leu Gln His Asn
        195                 200                 205

Glu Ile Gln Glu Val Gly Ser Ser Met Arg Gly Leu Arg Ser Leu Ile
    210                 215                 220

Leu Leu Asp Leu Ser Tyr Asn His Leu Arg Lys Val Pro Asp Gly Leu
225                 230                 235                 240

Pro Ser Ala Leu Glu Gln Leu Tyr Met Glu His Asn Asn Val Tyr Thr
                245                 250                 255

Val Pro Asp Ser Tyr Phe Arg Gly Ala Pro Lys Leu Leu Tyr Val Arg
            260                 265                 270

Leu Ser His Asn Ser Leu Thr Asn Asn Gly Leu Ala Ser Asn Thr Phe
        275                 280                 285
```

```
Asn Ser Ser Leu Leu Glu Leu Asp Leu Ser Tyr Asn Gln Leu Gln
    290                 295                 300

Lys Ile Pro Pro Val Asn Thr Asn Leu Glu Asn Leu Tyr Leu Gln Gly
305                 310                 315                 320

Asn Arg Ile Asn Glu Phe Ser Ile Ser Ser Phe Cys Thr Val Val Asp
                325                 330                 335

Val Val Asn Phe Ser Lys Leu Gln Val Leu Arg Leu Asp Gly Asn Glu
            340                 345                 350

Ile Lys Arg Ser Ala Met Pro Ala Asp Ala Pro Leu Cys Leu Arg Leu
                355                 360                 365

Ala Ser Leu Ile Glu Ile
            370
```

<210> SEQ ID NO 2
<211> LENGTH: 376
<212> TYPE: PRT
<213> ORGANISM: Homo sapiens

<400> SEQUENCE: 2

```
Met Gln Trp Thr Ser Leu Leu Leu Ala Gly Leu Phe Ser Leu Ser
1               5                   10                  15

Gln Ala Gln Tyr Glu Asp Asp Pro His Trp Trp Phe His Tyr Leu Arg
                20                  25                  30

Ser Gln Gln Ser Thr Tyr Tyr Asp Pro Tyr Asp Pro Tyr Pro Tyr Glu
            35                  40                  45

Thr Tyr Glu Pro Tyr Pro Tyr Gly Val Asp Glu Gly Pro Ala Tyr Thr
        50                  55                  60

Tyr Gly Ser Pro Ser Pro Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
                100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
        130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285
```

```
Thr Phe Asn Ser Ser Leu Leu Glu Leu Asp Leu Ser Tyr Asn Gln
    290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
                340                 345                 350

Asn Glu Ile Lys Arg Ser Ala Met Pro Ala Asp Ala Pro Leu Cys Leu
                355                 360                 365

Arg Leu Ala Ser Leu Ile Glu Ile
                370                 375

<210> SEQ ID NO 3
<211> LENGTH: 58
<212> TYPE: PRT
<213> ORGANISM: Homo sapiens

<400> SEQUENCE: 3

Tyr Leu Gln Gly Asn Arg Ile Asn Glu Phe Ser Ile Ser Ser Phe Cys
1               5                   10                  15

Thr Val Val Asp Val Val Asn Phe Ser Lys Leu Gln Val Leu Arg Leu
                20                  25                  30

Asp Gly Asn Glu Ile Lys Arg Ser Ala Met Pro Ala Asp Ala Pro Leu
                35                  40                  45

Cys Leu Arg Leu Ala Ser Leu Ile Glu Ile
                50                  55

<210> SEQ ID NO 4
<211> LENGTH: 361
<212> TYPE: PRT
<213> ORGANISM: Homo sapiens

<400> SEQUENCE: 4

Gln Trp Thr Ser Leu Leu Leu Ala Gly Leu Phe Ser Leu Ser Gln
1               5                   10                  15

Ala Gln Tyr Glu Asp Asp Pro His Trp Trp Phe His Tyr Leu Arg Ser
                20                  25                  30

Gln Gln Ser Thr Tyr Tyr Asp Pro Tyr Asp Pro Tyr Pro Tyr Glu Thr
                35                  40                  45

Tyr Glu Pro Tyr Pro Tyr Gly Val Asp Glu Gly Pro Ala Tyr Thr Tyr
                50                  55                  60

Gly Ser Pro Ser Pro Asp Pro Arg Asp Cys Pro Gln Glu Cys Asp
65                  70                  75                  80

Cys Pro Pro Asn Phe Pro Phe Val Pro Ser Arg Met Lys Tyr Val Tyr
                85                  90                  95

Phe Gln Asn Asn Gln Ile Thr Ser Ile Gln Glu Gly Val Phe Asp Asn
                100                 105                 110

Ala Thr Gly Leu Leu Trp Ile Ala Leu His Gly Asn Gln Ile Thr Ser
                115                 120                 125

Asp Lys Val Gly Arg Lys Val Phe Ser Lys Leu Arg His Leu Glu Arg
                130                 135                 140

Leu Tyr Leu Asp His Asn Asn Leu Thr Arg Met Pro Gly Pro Leu Pro
145                 150                 155                 160

Arg Ser Leu Arg Glu Leu His Leu Asp His Asn Gln Ile Ser Arg Val
                165                 170                 175
```

```
Pro Asn Asn Ala Leu Glu Gly Leu Glu Asn Leu Thr Ala Leu Tyr Leu
                180                 185                 190

Gln His Asn Glu Ile Gln Val Gly Ser Ser Met Arg Gly Leu Arg
            195                 200                 205

Ser Leu Ile Leu Leu Asp Leu Ser Tyr Asn His Leu Arg Lys Val Pro
    210                 215                 220

Asp Gly Leu Pro Ser Ala Leu Glu Gln Leu Tyr Met Glu His Asn Asn
225                 230                 235                 240

Val Tyr Thr Val Pro Asp Ser Tyr Phe Arg Gly Ala Pro Lys Leu Leu
                245                 250                 255

Tyr Val Arg Leu Ser His Asn Ser Leu Thr Asn Asn Gly Leu Ala Ser
            260                 265                 270

Asn Thr Phe Asn Ser Ser Ser Leu Leu Glu Leu Asp Leu Ser Tyr Asn
        275                 280                 285

Gln Leu Gln Lys Ile Pro Pro Val Asn Thr Asn Leu Glu Asn Leu Tyr
    290                 295                 300

Leu Gln Gly Asn Arg Ile Asn Glu Phe Ser Ile Ser Ser Phe Cys Thr
305                 310                 315                 320

Val Val Asp Val Val Asn Phe Ser Lys Leu Gln Val Leu Arg Leu Asp
                325                 330                 335

Gly Asn Glu Ile Lys Arg Ser Ala Met Pro Ala Asp Ala Pro Leu Cys
            340                 345                 350

Leu Arg Leu Ala Ser Leu Ile Glu Ile
        355                 360

<210> SEQ ID NO 5
<211> LENGTH: 201
<212> TYPE: PRT
<213> ORGANISM: Homo sapiens

<400> SEQUENCE: 5

Met Lys Met Thr Leu Ile Gly Gly Ser Thr Thr Ser Ala Ala Ser Ser
1               5                   10                  15

Pro Pro Thr Thr Ile Pro Met Thr Leu Thr Arg Met Arg Pro Thr Ser
            20                  25                  30

Leu Thr Pro Met Gly Trp Met Lys Gly Gln Pro Thr Pro Thr Ala Leu
        35                  40                  45

His Leu Asp His Asn Gln Ile Ser Arg Val Pro Asn Asn Ala Leu Glu
    50                  55                  60

Gly Leu Glu Asn Leu Thr Ala Met Tyr Cys Asp Asn Arg Asn Leu Lys
65                  70                  75                  80

Tyr Leu Pro Phe Val Pro Ser Arg Met Lys Tyr Val Tyr Phe Gln Asn
                85                  90                  95

Asn Gln Ile Thr Ser Ile Gln Glu Gly Val Phe Asp Asn Ala Thr Gly
            100                 105                 110

Leu Leu Trp Ile Ala Leu His Gly Asn Gln Ile Thr Ser Asp Lys Val
        115                 120                 125

Gly Arg Lys Val Phe Ser Lys Leu Arg His Leu Glu Arg Leu Tyr Leu
    130                 135                 140

Asp His Asn Asn Leu Thr Arg Met Pro Gly Pro Leu Pro Arg Ser Leu
145                 150                 155                 160

Arg Glu Leu His Leu Asp His Asn Gln Ile Pro Ala Thr Ala Pro Arg
                165                 170                 175

Asn Ala Thr Ala His Pro Thr Ser Pro Arg Pro Cys Thr Ser Asn Thr
```

```
                    180                 185                 190
Met Arg Ser Arg Lys Trp Ala Val Pro
        195                 200
```

<210> SEQ ID NO 6
<211> LENGTH: 287
<212> TYPE: PRT
<213> ORGANISM: Homo sapiens

<400> SEQUENCE: 6

```
Met Lys Met Thr Leu Ile Gly Gly Ser Thr Thr Ser Ala Ala Ser Ser
1               5                   10                  15

Pro Pro Thr Thr Ile Pro Met Thr Leu Thr Arg Met Arg Pro Thr Ser
            20                  25                  30

Leu Thr Pro Met Gly Trp Met Lys Gly Gln Pro Thr Pro Thr Ala Leu
        35                  40                  45

His Pro Leu Gln Ile Pro Ala Thr Ala Pro Arg Lys Val Phe Ser Lys
    50                  55                  60

Leu Arg His Leu Glu Arg Leu Tyr Leu Asp His Asn Asn Leu Thr Arg
65                  70                  75                  80

Met Pro Gly Pro Leu Pro Arg Ser Leu Arg Glu Leu His Leu Asp His
                85                  90                  95

Asn Gln Ile Ser Arg Val Pro Asn Asn Ala Leu Glu Gly Leu Glu Asn
            100                 105                 110

Leu Thr Ala Leu Tyr Leu Gln His Asn Glu Ile Gln Glu Val Gly Ser
        115                 120                 125

Ser Met Arg Gly Leu Arg Ser Leu Ile Leu Leu Asp Leu Ser Tyr Asn
    130                 135                 140

His Leu Arg Lys Val Pro Asp Gly Leu Pro Ser Ala Leu Glu Gln Leu
145                 150                 155                 160

Tyr Met Glu His Asn Asn Val Tyr Thr Val Pro Asp Ser Tyr Phe Arg
                165                 170                 175

Gly Ala Pro Lys Leu Leu Tyr Val Arg Leu Ser His Asn Ser Leu Thr
            180                 185                 190

Asn Asn Gly Leu Ala Ser Asn Thr Phe Asn Ser Ser Leu Leu Glu
        195                 200                 205

Leu Asp Leu Ser Tyr Asn Gln Leu Gln Lys Ile Pro Pro Val Asn Thr
    210                 215                 220

Asn Leu Glu Asn Leu Tyr Leu Gln Gly Asn Arg Ile Asn Glu Phe Ser
225                 230                 235                 240

Ile Ser Ser Phe Cys Thr Val Val Asp Val Asn Phe Ser Lys Leu
                245                 250                 255

Gln Val Leu Arg Leu Asp Gly Asn Glu Ile Lys Arg Ser Ala Met Pro
            260                 265                 270

Ala Asp Ala Pro Leu Cys Leu Arg Leu Ala Ser Leu Ile Glu Ile
        275                 280                 285
```

<210> SEQ ID NO 7
<211> LENGTH: 376
<212> TYPE: PRT
<213> ORGANISM: Homo sapiens

<400> SEQUENCE: 7

```
Met Gln Trp Thr Ser Leu Leu Leu Leu Ala Gly Leu Phe Ser Leu Ser
1               5                   10                  15

Gln Ala Gln Tyr Glu Asp Asp Pro His Trp Trp Phe His Tyr Leu Arg
```

```
                    20                  25                  30
Ser Gln Gln Ser Thr Tyr Tyr Asp Pro Tyr Asp Pro Tyr Glu
            35                  40                  45
Thr Tyr Glu Pro Tyr Pro Tyr Gly Val Asp Glu Gly Pro Ala Tyr Thr
    50                  55                  60
Tyr Gly Ser Pro Ser Pro Asp Pro Arg Asp Cys Pro Gln Glu Cys
65                  70                  75                  80
Asp Cys Pro Pro Asn Phe Pro Thr Ala Met Tyr Cys Asp Asn Arg Asn
                85                  90                  95
Leu Lys Tyr Leu Pro Phe Val Pro Ser Arg Met Lys Tyr Val Tyr Phe
            100                 105                 110
Gln Asn Asn Gln Ile Thr Ser Ile Gln Glu Gly Val Phe Asp Asn Ala
            115                 120                 125
Thr Gly Leu Leu Trp Ile Ala Leu His Gly Asn Gln Ile Thr Ser Asp
            130                 135                 140
Lys Val Gly Arg Lys Val Phe Ser Lys Leu Arg His Leu Glu Arg Leu
145                 150                 155                 160
Tyr Leu Asp His Asn Asn Leu Thr Arg Met Pro Gly Pro Leu Pro Arg
                165                 170                 175
Ser Leu Arg Glu Leu His Leu Asp His Asn Gln Ile Ser Arg Val Pro
            180                 185                 190
Asn Asn Ala Leu Glu Gly Leu Glu Asn Leu Thr Ala Leu Tyr Leu Gln
            195                 200                 205
His Asn Glu Ile Gln Glu Val Gly Ser Ser Met Arg Gly Leu Arg Ser
            210                 215                 220
Leu Ile Leu Leu Asp Leu Ser Tyr Asn His Leu Arg Lys Val Pro Asp
225                 230                 235                 240
Gly Leu Pro Ser Ala Leu Glu Gln Leu Tyr Met Glu His Asn Asn Val
                245                 250                 255
Tyr Thr Val Pro Asp Ser Tyr Phe Arg Gly Ala Pro Lys Leu Leu Tyr
            260                 265                 270
Val Arg Leu Ser His Asn Ser Leu Thr Asn Asn Gly Leu Ala Ser Asn
            275                 280                 285
Thr Phe Asn Ser Ser Ser Leu Leu Glu Leu Asp Leu Ser Tyr Asn Gln
            290                 295                 300
Leu Gln Lys Ile Pro Pro Val Asn Thr Asn Leu Glu Asn Leu Tyr Leu
305                 310                 315                 320
Gln Gly Asn Arg Ile Asn Glu Phe Ser Ile Ser Ser Phe Cys Thr Val
                325                 330                 335
Val Asp Val Val Asn Phe Ser Lys Leu Gln Val Leu Arg Leu Asp Gly
            340                 345                 350
Asn Glu Ile Lys Arg Ser Ala Met Pro Ala Asp Ala Pro Leu Cys Leu
            355                 360                 365
Arg Leu Ala Ser Leu Ile Glu Ile
        370                 375

<210> SEQ ID NO 8
<211> LENGTH: 376
<212> TYPE: PRT
<213> ORGANISM: Homo sapiens

<400> SEQUENCE: 8

Met Gln Trp Thr Ser Leu Leu Leu Leu Ala Gly Leu Phe Ser Leu Ser
1               5                   10                  15
```

-continued

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
            35                  40                  45

Thr Tyr Glu Pro Tyr Pro Tyr Gly Val Asp Glu Gly Pro Ala Tyr Thr
        50                  55                  60

Tyr Gly Ser Pro Ser Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
        130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
            195                 200                 205

His Asn Glu Ile Gln Glu Val Gly Ser Ser Met Arg Gly Leu Arg Ser
    210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
            275                 280                 285

Thr Phe Asn Ser Ser Ser Leu Leu Glu Leu Asp Leu Ser Tyr Asn Gln
        290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
            355                 360                 365

Arg Leu Ala Ser Leu Ile Glu Ile
        370                 375

<210> SEQ ID NO 9
<211> LENGTH: 377
<212> TYPE: PRT
<213> ORGANISM: Homo sapiens

<400> SEQUENCE: 9

Met Gln Trp Thr Ser Leu Leu Leu Leu Ala Gly Leu Phe Ser Leu Ser
1               5                   10                  15

Gln Ala Gln Tyr Glu Asp Asp Pro His Trp Trp Phe His Tyr Leu Arg
            20                  25                  30

Ser Gln Gln Ser Thr Tyr Tyr Asp Pro Tyr Asp Pro Tyr Pro Tyr Glu
            35                  40                  45

Thr Tyr Glu Pro Tyr Pro Tyr Gly Val Asp Glu Gly Pro Ala Tyr Thr
    50                  55                  60

Tyr Gly Ser Pro Ser Pro Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
            100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
            180                 185                 190

Asn Asn Ala Leu Glu Gly Leu Glu Asn Leu Thr Ala Leu Tyr Leu Gln
            195                 200                 205

His Asn Glu Ile Gln Glu Val Gly Ser Ser Met Arg Gly Leu Arg Ser
    210                 215                 220

Leu Tyr Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Ile Asn Asn
                245                 250                 255

Val Tyr Thr Val Pro Asp Ser Tyr Phe Arg Gly Ala Pro Lys Leu Leu
            260                 265                 270

Tyr Val Arg Leu Ser His Asn Ser Leu Thr Asn Asn Gly Leu Ala Ser
            275                 280                 285

Asn Thr Phe Asn Ser Ser Ser Leu Leu Glu Leu Asp Leu Ser Tyr Asn
    290                 295                 300

Gln Leu Gln Lys Ile Pro Pro Val Asn Thr Asn Leu Glu Asn Leu Tyr
305                 310                 315                 320

Leu Gln Gly Asn Arg Ile Asn Glu Phe Ser Ile Ser Ser Phe Cys Thr
                325                 330                 335

Val Val Asp Val Val Asn Phe Ser Gln Leu Gln Val Val Arg Leu Asp
            340                 345                 350

Gly Asn Glu Met Lys Arg Ser Ala Met Pro Ala Glu Ala Pro Leu Cys
            355                 360                 365

Leu Arg Leu Ala Ser Leu Ile Glu Ile
    370                 375

<210> SEQ ID NO 10
<211> LENGTH: 374
<212> TYPE: PRT
<213> ORGANISM: Homo sapiens

<400> SEQUENCE: 10

Met Gln Trp Ala Ser Leu Leu Leu Leu Ala Gly Leu Phe Ser Leu Ser

```
1               5                   10                  15
Gln Ala Gln Tyr Glu Asp Asp Pro His Trp Trp Phe His Tyr Leu Arg
                20                  25                  30

Ser Gln Gln Ser Thr Tyr Tyr Asp Pro Tyr Asp Pro Tyr Pro Tyr Glu
                35                  40                  45

Thr Tyr Glu Pro Tyr Pro Tyr Gly Val Asp Glu Gly Pro Ala Tyr Thr
                50                  55                  60

Tyr Gly Ser Pro Ser Pro Pro Asp Pro Arg Asp Cys Pro Gln Glu Cys
65                  70                  75                  80

Asp Cys Pro Pro Asn Phe Leu Thr Ala Met Tyr Cys Asp Asn Arg Asn
                85                  90                  95

Leu Lys Tyr Pro Phe Val Pro Ser Arg Met Lys Tyr Val Tyr Phe Gln
                100                 105                 110

Asn Asn Gln Ile Thr Ser Ile Gln Glu Gly Val Phe Asp Asn Ala Thr
                115                 120                 125

Gly Leu Leu Trp Ile Ala Leu His Gly Asn Gln Ile Thr Ser Asp Lys
                130                 135                 140

Val Gly Arg Lys Val Phe Ser Lys Leu Arg His Leu Glu Arg Leu Tyr
145                 150                 155                 160

Leu Asp His Asn Asn Leu Thr Arg Met Pro Gly Pro Leu Pro Arg Ser
                165                 170                 175

Leu Arg Glu Leu His Leu Asp His Asn Gln Ile Ser Arg Val Pro Asn
                180                 185                 190

Asn Ala Leu Glu Gly Leu Glu Asn Leu Thr Ala Leu Tyr Leu Gln His
                195                 200                 205

Asp Glu Ile Gln Glu Val Gly Ser Ser Met Arg Gly Leu Arg Ser Leu
                210                 215                 220

Ile Leu Leu Asp Leu Ser Tyr Asn His Leu Arg Lys Val Pro Asp Gly
225                 230                 235                 240

Leu Pro Ser Ala Leu Glu Gln Leu Tyr Met Glu His Asn Asn Val Tyr
                245                 250                 255

Thr Val Pro Asp Ser Tyr Phe Arg Gly Ala Pro Lys Leu Leu Tyr Val
                260                 265                 270

Arg Leu Ser His Asn Ser Leu Thr Asn Asn Gly Leu Ala Ser Asn Thr
                275                 280                 285

Phe Asn Ser Ser Ser Leu Glu Leu Asp Leu Ser Tyr Asn Gln Leu Gln
                290                 295                 300

Lys Ile Pro Pro Val Asn Thr Asn Leu Glu Asn Leu Tyr Leu Gln Gly
305                 310                 315                 320

Asn Arg Ile Asn Glu Phe Ser Ile Ser Ser Phe Cys Thr Val Val Asp
                325                 330                 335

Val Val Asn Phe Ser Lys Leu Gln Val Arg Leu Asp Gly Asn Glu
                340                 345                 350

Ile Lys Arg Ser Ala Met Pro Ala Asp Ala Pro Leu Cys Leu Arg Leu
                355                 360                 365

Ala Ser Leu Ile Glu Ile
                370

<210> SEQ ID NO 11
<211> LENGTH: 376
<212> TYPE: PRT
<213> ORGANISM: Homo sapiens

<400> SEQUENCE: 11
```

Met Gln Trp Thr Ser Leu Leu Leu Ala Gly Leu Phe Ser Leu Ser
1               5                   10                  15

Gln Ala Gln Tyr Glu Asp Pro His Trp Phe His Tyr Leu Arg
            20                  25                  30

Ser Gln Gln Ser Thr Tyr Tyr Asp Pro Tyr Asp Pro Tyr Glu
                35                  40                  45

Thr Tyr Glu Pro Tyr Pro Tyr Gly Val Asp Glu Gly Pro Ala Tyr Thr
        50                  55                  60

Tyr Gly Ser Pro Ser Pro Asp Pro Arg Asp Cys Pro Gln Glu Cys
65                  70                  75                  80

Asp Cys Pro Pro Asn Phe Pro Thr Ala Met Tyr Cys Asp Asn Arg Asn
                85                  90                  95

Leu Lys Tyr Leu Pro Phe Val Pro Ser Arg Met Lys Tyr Val Tyr Phe
                100                 105                 110

Gln Asn Asn Gln Ile Thr Ser Ile Gln Glu Gly Val Phe Asp Asn Ala
                115                 120                 125

Thr Gly Leu Leu Trp Ile Ala Leu His Gly Asn Gln Ile Thr Ser Asp
        130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
                180                 185                 190

Asn Asn Ala Leu Glu Gly Leu Glu Asn Leu Thr Ala Leu Tyr Leu Gln
        195                 200                 205

His Asn Glu Ile Gln Glu Val Gly Ser Ser Met Arg Gly Leu Arg Ser
        210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
            260                 265                 270

Val Arg Leu Ser His Asn Ser Leu Thr Asn Asn Gly Leu Ala Ser Asn
        275                 280                 285

Thr Phe Asn Ser Ser Ser Leu Leu Glu Leu Asp Leu Ser Tyr Asn Gln
        290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
                340                 345                 350

Asn Glu Ile Lys Arg Ser Ala Met Pro Ala Asp Ala Pro Leu Cys Leu
            355                 360                 365

Arg Leu Ala Ser Leu Ile Gly Ile
    370                 375

<210> SEQ ID NO 12
<211> LENGTH: 377
<212> TYPE: PRT
<213> ORGANISM: Homo sapiens

<400> SEQUENCE: 12

```
Met Gln Trp Thr Ser Leu Leu Leu Ala Gly Leu Phe Ser Leu Ser
1               5                   10                  15

Gln Ala Gln Tyr Glu Asp Pro His Trp Trp Phe His Tyr Leu Arg
            20                  25                  30

Ser Gln Gln Ser Thr Tyr Tyr Asp Pro Tyr Pro Tyr Pro Tyr Glu
        35                  40                  45

Thr Tyr Glu Pro Tyr Pro Tyr Gly Val Asp Glu Gly Pro Ala Tyr Thr
    50                  55                      60

Tyr Gly Ser Pro Ser Pro Pro Asp Pro Arg Asp Cys Pro Gln Glu Cys
65                  70                  75                  80

Asp Cys Pro Pro Asn Phe Pro Thr Ala Met Tyr Cys Asn Arg Asn
                85                  90                  95

Leu Lys Tyr Leu Pro Phe Val Pro Ser Arg Met Lys Tyr Val Tyr Phe
                100                 105                 110

Gln Asn Asn Gln Ile Thr Ser Ile Gln Glu Gly Val Phe Asp Asn Ala
            115                 120                 125

Thr Gly Leu Leu Trp Ile Ala Leu His Gly Asn Gln Ile Thr Ser Asp
    130                 135                 140

Lys Val Gly Arg Lys Val Phe Ser Lys Leu Arg His Leu Glu Arg Leu
145                 150                 155                 160

Tyr Leu Asp His Asn Asn Leu Thr Arg Met Pro Gly Pro Leu Pro Arg
                165                 170                 175

Ser Leu Arg Glu Leu His Leu Asp His Asn Gln Ile Ser Arg Val Pro
                180                 185                 190

Asn Asn Ala Leu Glu Gly Leu Glu Asn Leu Thr Ala Leu Tyr Leu Gln
            195                 200                 205

His Asn Glu Ile Gln Glu Val Gly Ser Ser Met Arg Gly Leu Arg Ser
            210                 215                 220

Leu Ile Leu Leu Asp Leu Ser Tyr Asn His Leu Arg Lys Val Pro Asp
225                 230                 235                 240

Gly Leu Pro Ser Ala Leu Glu Gln Leu Tyr Met Glu His Asn Asn Val
                245                 250                 255

Tyr Thr Val Pro Asp Ser Tyr Phe Arg Gly Ala Pro Lys Leu Leu Tyr
                260                 265                 270

Val Arg Leu Ser His Asn Ser Leu Thr Asn Asn Gly Leu Ala Ser Asn
                275                 280                 285

Thr Phe Asn Ser Ser Ser Leu Leu Glu Leu Asp Leu Ser Tyr Asn Gln
        290                 295                 300

Leu Gln Lys Ile Pro Pro Val Asn Thr Asn Leu Glu Asn Leu Tyr Leu
305                 310                 315                 320

Gln Gly Asn Arg Ile Asn Glu Phe Ser Ile Ser Ser Phe Cys Thr Val
                325                 330                 335

Val Asp Val Val Asn Phe Ser Lys Leu Gln Val Leu Arg Leu Asp Gly
            340                 345                 350

Asn Glu Ile Lys Arg Ser Ala Met Pro Ala Asp Ala Pro Leu Cys Leu
                355                 360                 365

Arg Leu Ala Ser Leu Ile Glu Ile Leu
    370                 375

<210> SEQ ID NO 13
<211> LENGTH: 16
<212> TYPE: PRT
<213> ORGANISM: Artificial Sequence
<220> FEATURE:
```

<223> OTHER INFORMATION: Description of Artificial Sequence:
     Fibromodulin peptide

<400> SEQUENCE: 13

Asn Arg Asn Leu Lys Tyr Leu Lys Pro Phe Val Pro Ser Arg Met Lys
1               5                   10                  15

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence:
     Fibromodulin peptide

<400> SEQUENCE: 14

Phe Gln Asn Asn Gln Ile Thr Ser Ile Gln Glu Gly Val Phe Asp Asn
1               5                   10                  15

Ala Thr Gly Leu Leu
            20

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:
     Fibromodulin peptide

<400> SEQUENCE: 15

Asn Arg Asn Leu Lys Tyr Leu Lys Pro Phe Val Pro Ser Arg Met Lys
1               5                   10                  15

<210> SEQ ID NO 16
<211> LENGTH: 64
<212> TYPE: PRT
<213> ORGANISM: Artificial Sequence
<220> FEATURE:
<223> OTHER INFORMATION: Description of Artificial Sequence:
     Fibromodulin peptide

<400> SEQUENCE: 16

Tyr Leu Arg Ser Gln Gln Ser Thr Tyr Tyr Asp Pro Tyr Asp Pro Tyr
1               5                   10                  15

Pro Tyr Glu Thr Tyr Glu Pro Tyr Pro Tyr Gly Val Asp Glu Gly Pro
                20                  25                  30

Ala Tyr Thr Tyr Gly Ser Pro Ser Pro Asp Pro Arg Asp Cys Pro
            35                  40                  45

Gln Glu Cys Asp Cys Pro Pro Asn Phe Pro Thr Ala Met Tyr Cys Asp
    50                  55                  60

<210> SEQ ID NO 17
<211> LENGTH: 40
<212> TYPE: PRT
<213> ORGANISM: Artificial Sequence
<220> FEATURE:
<223> OTHER INFORMATION: Description of Artificial Sequence:
     Fibromodulin peptide

<400> SEQUENCE: 17

Pro Tyr Gly Val Asp Glu Gly Pro Ala Tyr Thr Tyr Gly Ser Pro Ser
1               5                   10                  15

Pro Pro Asp Pro Arg Asp Cys Pro Gln Glu Cys Asp Cys Pro Pro Asn
                20                  25                  30

```
Phe Pro Thr Ala Met Tyr Cys Asp
        35                  40
```

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 18

```
Ser Arg Met Lys Tyr Val Tyr Phe Gln Asn Asn Gln Ile Thr Ser Ile
1               5                   10                  15

Gln Glu Gly Val Phe Asp Asn Ala Thr Gly Leu Leu Trp Ile Ala Leu
            20                  25                  30

His Gly Asn Gln Ile Thr Ser
        35
```

<210> SEQ ID NO 19
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 19

```
Asn Arg Asn Leu Lys Tyr Leu Pro Phe Val Pro Ser Arg Met Lys Tyr
1               5                   10                  15

Val Tyr Phe Gln Asn Asn Gln Ile Thr Ser Ile Gln Glu Gly Val Phe
            20                  25                  30

Asp Asn Ala Thr Gly Leu Leu Trp Ile Ala Leu His Gly Asn Gln Ile
        35                  40                  45

Thr Ser
    50
```

<210> SEQ ID NO 20
<211> LENGTH: 45
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 20

```
Asp Lys Val Gly Arg Lys Val Phe Ser Lys Leu Arg His Leu Glu Arg
1               5                   10                  15

Leu Tyr Leu Asp His Asn Asn Leu Thr Arg Met Pro Gly Pro Leu Pro
            20                  25                  30

Arg Ser Leu Arg Glu Leu His Leu Asp His Asn Gln Ile
        35                  40                  45
```

<210> SEQ ID NO 21
<211> LENGTH: 68
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 21

```
Ser Arg Val Pro Asn Asn Ala Leu Glu Gly Leu Glu Asn Leu Thr Ala
1               5                   10                  15
```

```
Leu Tyr Leu Gln His Asn Glu Ile Gln Glu Val Gly Ser Ser Met Arg
            20                  25                  30

Gly Leu Arg Ser Leu Ile Leu Leu Asp Leu Ser Tyr Asn His Leu Arg
        35                  40                  45

Lys Val Pro Asp Gly Leu Pro Ser Ala Leu Glu Gln Leu Tyr Met Glu
    50                  55                  60

His Asn Asn Val
65

<210> SEQ ID NO 22
<211> LENGTH: 69
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 22

Tyr Thr Val Pro Asp Ser Tyr Phe Arg Gly Ala Pro Lys Leu Leu Tyr
1               5                   10                  15

Val Arg Leu Ser His Asn Ser Leu Thr Asn Asn Gly Leu Ala Ser Asn
            20                  25                  30

Thr Phe Asn Ser Ser Leu Leu Glu Leu Asp Leu Ser Tyr Asn Gln
        35                  40                  45

Leu Gln Lys Ile Pro Pro Val Asn Thr Asn Leu Glu Asn Leu Tyr Leu
    50                  55                  60

Gln Gly Asn Arg Ile
65

<210> SEQ ID NO 23
<211> LENGTH: 51
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 23

Asn Glu Phe Ser Ile Ser Ser Phe Cys Thr Val Val Asp Val Val Asn
1               5                   10                  15

Phe Ser Lys Leu Gln Val Leu Arg Leu Asp Gly Asn Glu Ile Lys Arg
            20                  25                  30

Ser Ala Met Pro Ala Asp Ala Pro Leu Cys Leu Arg Leu Ala Ser Leu
        35                  40                  45

Ile Glu Ile
    50

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 24

Gln Trp Thr Ser Leu Leu Leu Ala Gly Leu Phe Ser Leu Ser Gln
1               5                   10                  15

Ala Gln Tyr Glu Asp Asp Pro His Trp Trp Phe His Tyr Leu Arg Ser
            20                  25                  30
```

Gln Gln Ser Thr Tyr Tyr Asp Pro
        35                  40

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 25

Asp Asp Pro His Trp Trp Phe His Tyr Leu Arg Ser Gln Gln Ser Thr
1               5                   10                  15

Tyr Tyr Asp Pro Tyr Asp Pro Tyr Pro Tyr Glu Thr Tyr Glu Pro Tyr
                20                  25                  30

Pro Tyr Gly Val Asp Glu Gly Pro
        35                  40

<210> SEQ ID NO 26
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 26

Asp Pro Arg Asp Cys Pro Gln Glu Cys Asp Cys Pro Pro Asn Phe Pro
1               5                   10                  15

Thr Ala Met Tyr Cys Asp Asn Arg Asn Leu Lys Tyr Leu Pro Phe Val
                20                  25                  30

Pro Ser Arg Met Lys Tyr Val Tyr Phe Gln Asn Asn Gln Ile Thr Ser
        35                  40                  45

Ile Gln
    50

<210> SEQ ID NO 27
<211> LENGTH: 51
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 27

Tyr Gly Ser Pro Ser Pro Pro Asp Pro Arg Asp Cys Pro Gln Glu Cys
1               5                   10                  15

Asp Cys Pro Pro Asn Phe Pro Thr Ala Met Tyr Cys Asp Asn Arg Asn
                20                  25                  30

Leu Lys Tyr Leu Pro Phe Val Pro Ser Arg Met Lys Tyr Val Tyr Phe
        35                  40                  45

Gln Asn Asn
    50

<210> SEQ ID NO 28
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 28

```
Phe Pro Thr Ala Met Tyr Cys Asp Asn Arg Asn Leu Lys Tyr Leu Pro
1               5                   10                  15

Phe Val Pro Ser Arg Met Lys Tyr Val Tyr Phe Gln Asn Asn Gln Ile
                20                  25                  30

Thr Ser Ile Gln Glu Gly Val Phe Asp Asn Ala Thr Gly Leu Leu Trp
            35                  40                  45

Ile Ala
    50

<210> SEQ ID NO 29
<211> LENGTH: 58
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 29

Leu Leu Trp Ile Ala Leu His Gly Asn Gln Ile Thr Ser Asp Lys Val
1               5                   10                  15

Gly Arg Lys Val Phe Ser Lys Leu Arg His Leu Glu Arg Leu Tyr Leu
                20                  25                  30

Asp His Asn Asn Leu Thr Arg Met Pro Gly Pro Leu Pro Arg Ser Leu
            35                  40                  45

Arg Glu Leu His Leu Asp His Asn Gln Ile
            50                  55

<210> SEQ ID NO 30
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 30

Ala Tyr Thr Tyr Gly Ser Pro Ser Pro Pro Asp Pro Arg Asp Cys Pro
1               5                   10                  15

Gln Glu Cys Asp Cys Pro Pro Asn Phe Pro Thr Ala Met Tyr Cys Asp
                20                  25                  30

Asn Arg Asn Leu Lys Tyr Leu Pro Phe Val Pro Ser Arg Met Lys Tyr
            35                  40                  45

Val Tyr
    50

<210> SEQ ID NO 31
<211> LENGTH: 47
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 31

Ser Arg Val Pro Asn Asn Ala Leu Glu Gly Leu Glu Asn Leu Thr Ala
1               5                   10                  15

Leu Tyr Leu Gln His Asn Glu Ile Gln Glu Val Gly Ser Ser Met Arg
                20                  25                  30

Gly Leu Arg Ser Leu Ile Leu Leu Asp Leu Ser Tyr Asn His Leu
            35                  40                  45
```

```
<210> SEQ ID NO 32
<211> LENGTH: 46
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 32

Arg Lys Val Pro Asp Gly Leu Pro Ser Ala Leu Glu Gln Leu Tyr Met
1               5                   10                  15

Glu His Asn Asn Val Tyr Thr Val Pro Asp Ser Tyr Phe Arg Gly Ala
                20                  25                  30

Pro Lys Leu Leu Tyr Val Arg Leu Ser His Asn Ser Leu Thr
            35                  40                  45

<210> SEQ ID NO 33
<211> LENGTH: 44
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 33

Asn Asn Gly Leu Ala Ser Asn Thr Phe Asn Ser Ser Leu Leu Glu
1               5                   10                  15

Leu Asp Leu Ser Tyr Asn Gln Leu Gln Lys Ile Pro Pro Val Asn Thr
                20                  25                  30

Asn Leu Glu Asn Leu Tyr Leu Gln Gly Asn Arg Ile
            35                  40

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 34

Thr Ser Ile Gln Glu Gly Val Phe Asp Asn Ala Thr Gly Leu Leu Trp
1               5                   10                  15

Ile Ala Leu His Gly Asn Gln Ile Thr Ser Asp Lys Val Gly Arg Lys
                20                  25                  30

Val Phe Ser Lys Leu Arg His Leu Glu Arg Leu Tyr Leu Asp His Asn
            35                  40                  45

Asn Leu
    50

<210> SEQ ID NO 35
<211> LENGTH: 47
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 35

Thr Arg Met Pro Gly Pro Leu Pro Arg Ser Leu Arg Glu Leu His Leu
1               5                   10                  15

Asp His Asn Gln Ile Ser Arg Val Pro Asn Asn Ala Leu Glu Gly Leu
                20                  25                  30
```

Glu Asn Leu Thr Ala Leu Tyr Leu Gln His Asn Glu Ile Gln Glu
            35                  40                  45

<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 36

Val Gly Ser Ser Met Arg Gly Leu Arg Ser Leu Ile Leu Leu Asp Leu
1               5                   10                  15

Ser Tyr Asn His Leu Arg Lys Val Pro Asp Gly Leu Pro Ser Ala Leu
            20                  25                  30

Glu Gln Leu Tyr Met Glu His Asn Asn Val
            35                  40

<210> SEQ ID NO 37
<211> LENGTH: 49
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 37

Tyr Thr Val Pro Asp Ser Tyr Phe Arg Gly Ala Pro Lys Leu Leu Tyr
1               5                   10                  15

Val Arg Leu Ser His Asn Ser Leu Thr Asn Asn Gly Leu Ala Ser Asn
            20                  25                  30

Thr Phe Asn Ser Ser Ser Leu Leu Glu Leu Asp Leu Ser Tyr Asn Gln
            35                  40                  45

Leu

<210> SEQ ID NO 38
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 38

Gln Lys Ile Pro Pro Val Asn Thr Asn Leu Glu Asn Leu Tyr Leu Gln
1               5                   10                  15

Gly Asn Arg Ile Asn Glu Phe Ser Ile Ser Ser Phe Cys Thr Val Val
            20                  25                  30

Asp Val Val Asn Phe Ser Lys Leu Gln Val Leu Arg Leu Asp Gly Asn
            35                  40                  45

Glu Ile
    50

<210> SEQ ID NO 39
<211> LENGTH: 58
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 39

```
Asp Lys Val Gly Arg Lys Val Phe Ser Lys Leu Arg His Leu Glu Arg
1               5                   10                  15

Leu Tyr Leu Asp His Asn Asn Leu Thr Arg Met Pro Gly Pro Leu Pro
            20                  25                  30

Arg Ser Leu Arg Glu Leu His Leu Asp His Asn Gln Ile Ser Arg Val
        35                  40                  45

Pro Asn Asn Ala Leu Glu Gly Leu Glu Asn
    50                  55

<210> SEQ ID NO 40
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 40

Asn Ala Thr Gly Leu Leu Trp Ile Ala Leu His Gly Asn Gln Ile Thr
1               5                   10                  15

Ser Asp Lys Val Gly Arg Lys Val Phe Ser Lys Leu Arg His Leu Glu
            20                  25                  30

Arg Leu Tyr Leu Asp His Asn Asn
        35                  40

<210> SEQ ID NO 41
<211> LENGTH: 75
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 41

Asn Ala Thr Gly Leu Leu Trp Ile Ala Leu His Gly Asn Gln Ile Thr
1               5                   10                  15

Ser Asp Lys Val Gly Arg Lys Val Phe Ser Lys Leu Arg His Leu Glu
            20                  25                  30

Arg Leu Tyr Leu Asp His Asn Asn Leu Thr Arg Met Pro Gly Pro Leu
        35                  40                  45

Pro Arg Ser Leu Arg Glu Leu His Leu Asp His Asn Gln Ile Ser Arg
    50                  55                  60

Val Pro Asn Asn Ala Leu Glu Gly Leu Glu Asn
65                  70                  75

<210> SEQ ID NO 42
<211> LENGTH: 91
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 42

Asn Leu Thr Ala Leu Tyr Leu Gln His Asn Glu Ile Gln Glu Val Gly
1               5                   10                  15

Ser Ser Met Arg Gly Leu Arg Ser Leu Ile Leu Leu Asp Leu Ser Tyr
            20                  25                  30

Asn His Leu Arg Lys Val Pro Asp Gly Leu Pro Ser Ala Leu Glu Gln
        35                  40                  45
```

Leu Tyr Met Glu His Asn Asn Val Tyr Thr Val Pro Asp Ser Tyr Phe
            50                  55                  60

Arg Gly Ala Pro Lys Leu Leu Tyr Val Arg Leu Ser His Asn Ser Leu
65                  70                  75                  80

Thr Asn Asn Gly Leu Ala Ser Asn Thr Phe Asn
                85                  90

<210> SEQ ID NO 43
<211> LENGTH: 68
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 43

Thr Arg Met Pro Gly Pro Leu Pro Arg Ser Leu Arg Glu Leu His Leu
1               5                   10                  15

Asp His Asn Gln Ile Ser Arg Val Pro Asn Asn Ala Leu Glu Gly Leu
                20                  25                  30

Glu Asn Leu Thr Ala Leu Tyr Leu Gln His Asn Glu Ile Gln Glu Val
            35                  40                  45

Gly Ser Ser Met Arg Gly Leu Arg Ser Leu Ile Leu Leu Asp Leu Ser
    50                  55                  60

Tyr Asn His Leu
65

<210> SEQ ID NO 44
<211> LENGTH: 56
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 44

Arg Lys Val Pro Asp Gly Leu Pro Ser Ala Leu Glu Gln Leu Tyr Met
1               5                   10                  15

Glu His Asn Asn Val Tyr Thr Val Pro Asp Ser Tyr Phe Arg Gly Ala
                20                  25                  30

Pro Lys Leu Leu Tyr Val Arg Leu Ser His Asn Ser Leu Thr Asn Asn
            35                  40                  45

Gly Leu Ala Ser Asn Thr Phe Asn
    50                  55

<210> SEQ ID NO 45
<211> LENGTH: 44
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 45

Asn Ser Ser Ser Leu Leu Glu Leu Asp Leu Ser Tyr Asn Gln Leu Gln
1               5                   10                  15

Lys Ile Pro Pro Val Asn Thr Asn Leu Glu Asn Leu Tyr Leu Gln Gly
                20                  25                  30

Asn Arg Ile Asn Glu Phe Ser Ile Ser Ser Phe Cys
            35                  40

-continued

```
<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 46

Cys Thr Val Val Asp Val Val Asn Phe Ser Lys Leu Gln Val Leu Arg
1               5                   10                  15

Leu Asp Gly Asn Glu Ile Lys Arg Ser Ala Met Pro Ala Asp Ala Pro
            20                  25                  30

Leu Cys

<210> SEQ ID NO 47
<211> LENGTH: 62
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 47

Gln Lys Ile Pro Pro Val Asn Thr Asn Leu Glu Asn Leu Tyr Leu Gln
1               5                   10                  15

Gly Asn Arg Ile Asn Glu Phe Ser Ile Ser Ser Phe Cys Thr Val Val
            20                  25                  30

Asp Val Val Asn Phe Ser Lys Leu Gln Val Leu Arg Leu Asp Gly Asn
        35                  40                  45

Glu Ile Lys Arg Ser Ala Met Pro Ala Asp Ala Pro Leu Cys
    50                  55                  60

<210> SEQ ID NO 48
<211> LENGTH: 42
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 48

Cys Pro Gln Glu Cys Asp Cys Pro Pro Asn Phe Pro Thr Ala Met Tyr
1               5                   10                  15

Cys Asp Asn Arg Asn Leu Lys Tyr Leu Pro Phe Val Pro Ser Arg Met
            20                  25                  30

Lys Tyr Val Tyr Phe Gln Asn Asn Gln Ile
        35                  40

<210> SEQ ID NO 49
<211> LENGTH: 62
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 49

Ala Thr Gly Leu Leu Trp Ile Ala Leu His Gly Asn Gln Ile Thr Ser
1               5                   10                  15

Asp Lys Val Gly Arg Lys Val Phe Ser Lys Leu Arg His Leu Glu Arg
            20                  25                  30

Leu Tyr Leu Asp His Asn Asn Leu Thr Arg Met Pro Gly Pro Leu Pro
```

```
                    35                  40                  45

Arg Ser Leu Arg Glu Leu His Leu Asp His Asn Gln Ile Ser
     50                  55                  60

<210> SEQ ID NO 50
<211> LENGTH: 49
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 50

Asn Leu Thr Arg Met Pro Gly Pro Leu Pro Arg Ser Leu Arg Glu Leu
1               5                   10                  15

His Leu Asp His Asn Gln Ile Ser Arg Val Pro Asn Asn Ala Leu Glu
            20                  25                  30

Gly Leu Glu Asn Leu Thr Ala Leu Tyr Leu Gln His Asn Glu Ile Gln
        35                  40                  45

Glu

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 51

Asn Leu Thr Arg Met Pro Gly Pro Leu Pro Arg Ser Leu Arg Glu Leu
1               5                   10                  15

His Leu Asp His Asn Gln Ile Ser Arg Val Pro Asn Asn Ala Leu Glu
            20                  25                  30

Gly Leu Glu Asn
        35

<210> SEQ ID NO 52
<211> LENGTH: 47
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 52

Gly Leu Pro Ser Ala Leu Glu Gln Leu Tyr Met Glu His Asn Asn Val
1               5                   10                  15

Tyr Thr Val Pro Asp Ser Tyr Phe Arg Gly Ala Pro Lys Leu Leu Tyr
            20                  25                  30

Val Arg Leu Ser His Asn Ser Leu Thr Asn Asn Gly Leu Ala Ser
        35                  40                  45

<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 53

His Leu Asp His Asn Gln Ile Ser Arg Val Pro Asn Asn Ala Leu Glu
```

```
                1               5                  10                  15
Gly Leu Glu Asn Leu Thr Ala Leu Tyr Leu Gln His Asn Glu Ile Gln
                20                  25                  30
Glu Val Gly Ser Ser Met Arg Gly
        35                  40

<210> SEQ ID NO 54
<211> LENGTH: 34
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 54

Phe Ser Lys Leu Gln Val Leu Arg Leu Asp Gly Asn Glu Ile Lys Arg
1               5                   10                  15
Ser Ala Met Pro Ala Asp Ala Pro Leu Cys Leu Arg Leu Ala Ser Leu
                20                  25                  30
Ile Glu

<210> SEQ ID NO 55
<211> LENGTH: 39
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 55

Pro Asn Asn Ala Leu Glu Gly Leu Glu Asn Leu Thr Ala Leu Tyr Leu
1               5                   10                  15
Gln His Asn Glu Ile Gln Glu Val Gly Ser Ser Met Arg Gly Leu Arg
                20                  25                  30
Ser Leu Ile Leu Leu Asp Leu
        35

<210> SEQ ID NO 56
<211> LENGTH: 49
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 56

Pro Asp Gly Leu Pro Ser Ala Leu Glu Gln Leu Tyr Met Glu His Asn
1               5                   10                  15
Asn Val Tyr Thr Val Pro Asp Ser Tyr Phe Arg Gly Ala Pro Lys Leu
                20                  25                  30
Leu Tyr Val Arg Leu Ser His Asn Ser Leu Thr Asn Asn Gly Leu Ala
        35                  40                  45
Ser

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 57
```

```
Leu Leu Asp Leu Ser Tyr Asn His Leu Arg Lys Val Pro Asp Gly Leu
1               5                   10                  15

Pro Ser Ala Leu Glu Gln Leu Tyr Met Glu His Asn Asn Val Tyr Thr
            20                  25                  30

Val Pro Asp Ser Tyr Phe Arg Gly
            35                  40

<210> SEQ ID NO 58
<211> LENGTH: 50
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 58

Ser Lys Leu Arg His Leu Glu Arg Leu Tyr Leu Asp His Asn Asn Leu
1               5                   10                  15

Thr Arg Met Pro Gly Pro Leu Pro Arg Ser Leu Arg Glu Leu His Leu
            20                  25                  30

Asp His Asn Gln Ile Ser Arg Val Pro Asn Asn Ala Leu Glu Gly Leu
            35                  40                  45

Glu Asn
    50

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 59

Leu Arg Ser Leu Ile Leu Leu Asp Leu Ser Tyr Asn His Leu Arg Lys
1               5                   10                  15

Val Pro Asp Gly Leu Pro Ser Ala Leu Glu Gln Leu Tyr Met Glu His
            20                  25                  30

Asn Asn Val Tyr Thr Val Pro Asp
            35                  40

<210> SEQ ID NO 60
<211> LENGTH: 40
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 60

Tyr Val Arg Leu Ser His Asn Ser Leu Thr Asn Asn Gly Leu Ala Ser
1               5                   10                  15

Asn Thr Phe Asn Ser Ser Ser Leu Leu Glu Leu Asp Leu Ser Tyr Asn
            20                  25                  30

Gln Leu Gln Lys Ile Pro Pro Val
            35                  40

<210> SEQ ID NO 61
<211> LENGTH: 40
<212> TYPE: PRT
<213> ORGANISM: Artificial Sequence
<220> FEATURE:
```

```
<223> OTHER INFORMATION: Description of Artificial Sequence:
      Fibromodulin peptide

<400> SEQUENCE: 61

Asn Asn Gly Leu Ala Ser Asn Thr Phe Asn Ser Ser Leu Leu Glu
1               5                   10                  15

Leu Asp Leu Ser Tyr Asn Gln Leu Gln Lys Ile Pro Pro Val Asn Thr
            20                  25                  30

Asn Leu Glu Asn Leu Tyr Leu Gln
        35                  40

<210> SEQ ID NO 62
<211> LENGTH: 51
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 62

His Trp Trp Phe His Tyr Leu Arg Ser Gln Gln Ser Thr Tyr Tyr Asp
1               5                   10                  15

Pro Tyr Asp Pro Tyr Pro Tyr Glu Thr Tyr Glu Pro Tyr Pro Tyr Gly
            20                  25                  30

Val Asp Glu Gly Pro Ala Tyr Thr Tyr Gly Ser Pro Ser Pro Pro Asp
        35                  40                  45

Pro Arg Asp
        50

<210> SEQ ID NO 63
<211> LENGTH: 39
<212> TYPE: PRT
<213> ORGANISM: Artificial Sequence
<220> FEATURE:
<223> OTHER INFORMATION: Description of Artificial Sequence:
      Fibromodulin peptide

<400> SEQUENCE: 63

His Asn Ser Leu Thr Asn Asn Gly Leu Ala Ser Asn Thr Phe Asn Ser
1               5                   10                  15

Ser Ser Leu Leu Glu Leu Asp Leu Ser Tyr Asn Gln Leu Gln Lys Ile
            20                  25                  30

Pro Pro Val Asn Thr Asn Leu
        35

<210> SEQ ID NO 64
<211> LENGTH: 112
<212> TYPE: PRT
<213> ORGANISM: Homo sapiens

<400> SEQUENCE: 64

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80
```

```
Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 65
<211> LENGTH: 100
<212> TYPE: PRT
<213> ORGANISM: Homo sapiens

<400> SEQUENCE: 65

Gln Asp Asn Cys Cys Leu Arg Pro Leu Tyr Ile Asp Phe Lys Arg Asp
1               5                   10                  15

Leu Gly Trp Lys Trp Ile His Glu Pro Lys Gly Tyr Asn Ala Asn Phe
            20                  25                  30

Cys Ala Gly Ala Cys Pro Tyr Leu Trp Ser Ser Asp Thr Gln His Arg
            35                  40                  45

Val Leu Ser Leu Tyr Asn Thr Ile Asn Pro Glu Ala Ser Ala Ser Pro
50                  55                  60

Cys Cys Val Ser Gln Asp Leu Glu Pro Leu Thr Ile Leu Tyr Tyr Ile
65                  70                  75                  80

Gly Lys Thr Pro Lys Ile Glu Gln Leu Ser Asn Met Ile Val Lys Ser
                85                  90                  95

Cys Lys Cys Ser
            100

<210> SEQ ID NO 66
<211> LENGTH: 99
<212> TYPE: PRT
<213> ORGANISM: Homo sapiens

<400> SEQUENCE: 66

Asn Cys Cys Val Arg Pro Leu Tyr Ile Asp Phe Arg Gln Asp Leu Gly
1               5                   10                  15

Trp Lys Trp Val His Glu Pro Lys Gly Tyr Tyr Ala Asn Phe Cys Ser
            20                  25                  30

Gly Pro Cys Pro Tyr Leu Arg Ser Ala Asp Thr Thr His Ser Thr Val
            35                  40                  45

Leu Gly Leu Tyr Asn Thr Leu Asn Pro Glu Ala Ser Ala Ser Pro Cys
50                  55                  60

Cys Val Pro Gln Asp Leu Glu Pro Leu Thr Ile Leu Tyr Tyr Val Gly
65                  70                  75                  80

Arg Thr Pro Lys Val Glu Gln Leu Ser Asn Met Val Val Lys Ser Cys
                85                  90                  95

Lys Cys Ser
```

METHODS AND COMPOSITIONS FOR MODULATING MYOFIBROBLAST ACTIVITIES

CROSS-REFERENCE TO RELATED APPLICATIONS

This application is a continuation-in-part of U.S. patent application Ser. No. 16/405,782, filed May 7, 2019, which, in turn, is a continuation of U.S. patent application Ser. No. 15/673,880, filed Aug. 10, 2017, which is a divisional application of U.S. patent application Ser. No. 14/106,617 filed Dec. 13, 2013, issued as U.S. Pat. No. 9,744,214, which is a continuation of PCT/US2012/042517, filed Jun. 14, 2012, which claims the benefit of U.S. provisional application No. 61/497,397, filed Jun. 15, 2011, all of which are hereby incorporated by reference herein in their entirety.

REFERENCE TO A SEQUENCE LISTING

The instant application contains a Sequence Listing which has been filed electronically in ASCII format and is hereby incorporated by reference in its entirety. Said ASCII copy, created on Jul. 6, 2020, is named 74578-1036-Sequence-Listing_CRF.txt and is 65,934 bytes in size.

FIELD OF THE INVENTION

The present invention generally relates to methods and compositions for treating or ameliorating a condition associated with increased or decreased myofibroblast activities and use thereof.

BACKGROUND OF THE INVENTION

Excessive or deficient myofibroblast activity is associated with many diseases and biological and medical processes. Such diseases include those shown in Table 1*.

| Tissue or Organ | Activation/Proliferation | Deletion or Damage |
|---|---|---|
| Skin<br>Granulation tissue | Scleroderma: keloid: Dupuytren's contracture<br>(72, 213, 224); psoriasis (63) | |
| Pericyte | Atherosclerosis and restenosis (149, 159)<br>hypertension (208) | Microaneurysms, edema, and hemorrhage (26, 239) |
| Mouth<br>Periodontal ligament<br>Gingival myofibroblasts | Periodontal disease (136, 214)<br>Gingival hypertrophy secondary to<br>drugs (cyclosporine and Dilantin) (135, 136, 212, 214, 216) | |
| Eye<br>Orbital fibroblast<br>Retinal myofibroblast<br>Anterior capsule of lens<br>Corneal myofibroblast | Exophthalmos (proptosis) of Grave's disease<br>(9, 221, 254)<br>Proliferative vitreoretinopathy (253)<br>Anterior capsular cataract (172, 217)<br>Corneal scarring (184) | Diabetic microaneurysm (26, 142, 239) |
| Heart and pericardium | Myocardial fibrosis, atherosclerosis, and coronary artery restenosis (35, 149, 159, 258) | |
| Kidney<br>Mesangial cell<br>Interstitial cell | Proliferative and sclerosing glomerulonephritis<br>(108, 184, 239)<br>Renal tubulointerstitial fibrosis (171, 177, 198, 239) | Absence of glomerular structure (141, 234) |
| Liver<br>Perisinusoidal<br>Stellate (Ito cell) | Fibrosis and cirrhosis (72, 88, 150)<br>Ischemia reperfusion injury of hepatic transplantation (206)<br>Necrotizing hepatitis (62) | |
| Pancreas<br>Periacinal stellate cell | Pancreatic fibrosis (4, 8) | |
| Lung<br>Interstitial contractile cell | Pulmonary interstitial fibrosis, idiopathic and drug-induced; sarcoidosis (105, 209, 214) | Emphysema (25) |
| Stomach and intestine<br>Interstitial cell of Cajal<br>Subepithelial myofibroblast | Collagenous colitis; villous atrophy and crypt hyperplasia; fibrosis of Crohn's disease (2, 86, 114, 131, 153)<br>Healing gastric ulcer | Abnormal intestinal motility; hypertrophic pyloric stenosis; Hirschsprung's disease; megacolon of piebaldism; idiopathic pseudo-obstruction (33, 52, 115, 183, 212, 243, 248, 249) |
| Brain<br>Astrocyte | Produce glial scar tissue (166) | Human immunodeficiency virus-associated cognitive motor disease; spongiform encephalopathy (166) |

-continued

| Tissue or Organ | Activation/Proliferation | Deletion or Damage |
|---|---|---|
| Breast Stromal myofibroblast | Fibrocystic disease; desmoplastic reaction to breast cancer (73, 214) | |
| Bone marrow Stromal myofibroblast | Fibrosis in myelodysplasia and neoplastic diseases (182, 218) | Aplastic anemia (182, 218) |
| Joint Synoviocyte | Rheumatoid pannus formation (11) | |

*See Table 5 of Powell, et al., Myofibroblasts. I. Paracrine cells important in health and disease, Am J Physiol Cell Physiol Jul. 1, 1999 vol. 277 no. 1 C1-C19, references shown in this table refers to the articles cited in Powell, et al.

Thus far, there are no effective ways of treating or ameliorating many of the conditions associated with excessive or deficient myofibroblast activities.

Therefore, there is a need for methods and compositions for modulating myofibroblast activity.

The embodiments below address the above-identified issues and needs.

SUMMARY OF THE INVENTION

In one aspect of the present invention, it is provided method for treating or ameliorating a disorder associated with increased or decreased myofibroblast activity, which method comprising modulating the myofibroblast level in a subject in need thereof by modulating fibromodulin level in the subject. The subject can be a mammal, e.g., a patient or an animal.

In some embodiments of the method, modulating myofibroblast level comprises increasing fibromodulin level.

In some embodiments of the method, modulating myofibroblast level comprises decreasing fibromodulin level.

In some embodiments of the method, modulating fibromodulin level in the subject comprises effectively modulating the level of fibromodulin activity so as to modulate activities of a myofibroblast apoptosis inducing agent. Such myofibroblast apoptosis inducing agent can be, e.g., interleukin-1β (IL-1β).

In some embodiments of the method, modulating myofibroblast level comprises applying to the subject an effective amount of fibromodulin for promoting myofibroblast differentiation and apoptosis thereby increasing the myofibroblast level in the subject where early, but short duration myofibroblast activity is effective for the disorder or inhibiting prolonged myofibroblast activity in the subject where the disorder is associated with prolonged myofibroblast activity, wherein the myofibroblast differentiation is induced by a myofibroblast inducing agent.

In some embodiments of the method, modulating myofibroblast level comprises blocking fibromodulin activity so as to prolong myofibroblast activity.

In some embodiments of the method, blocking fibromodulin activity comprises administering to the subject anti-sense oligonucleotides, antibodies, peptides that inhibit fibromodulin activities, and combinations thereof.

In some embodiments of the method, the disorder is atherosclerosis, restenosis, cirrhosis, hemorrhage, microaneurysms, wounds with impaired cell motility, diabetic wounds, wounds with impaired tensile strength, wounds in patients on corticosteroids, wounds in olders, emphysema, interstitial lung diseases, asthma, Dupuytren's contracture, or another disease in Table 1.

In some embodiments of the method, optionally in combination with any or all of the above embodiments, the myofibroblast differentiation inducing agent is TGF-β1.

In another aspect of the present invention, it is provided a composition, which composition comprising an effective amount of fibromodulin peptide for promoting myofibroblast differentiation and apoptosis in a subject having a disorder associated with myofibroblast activity, wherein the composition is in a controlled release formulation that provides controlled release of fibromodulin peptide, and wherein the composition further comprises TGF-β1.

In some embodiments of the method, optionally in combination with any or all of the above embodiments, the composition further comprises an excipient, wherein the formulation is a formulation for topical, transdermal, intradermal, or microneedle delivery.

In some embodiments of the method, optionally in combination with any or all of the above embodiments, the excipient comprises a polymer.

In some embodiments of the method, optionally in combination with any or all of the above embodiments, the composition is formulated in a dosage form selected from an extract, pills, tablets, microparticles, capsules, oral liquid.

The composition of claim 1, further comprising an agent selected from the group consisting of antibiotics, antifungals, virucidals and immunostimulants.

In some embodiments of the method, optionally in combination with any or all of the above embodiments, the effective amount is effective for bone formation.

In some embodiments of the method, optionally in combination with any or all of the above embodiments, the excipient is a carrier selected from collagen, atelocollagen, hydroxyapatite, and a polymer.

In some embodiments of the method, optionally in combination with any or all of the above embodiments, the polymer is a bioabsorbable polymer.

In some embodiments of the method, optionally in combination with any or all of the above embodiments, the polymer is polylactide (PLA), or poly(lactic acid-co-glycolic acid).

In another aspect of the present invention, it is provided a method, which method comprises applying a composition to the medical device, the composition comprising an effective amount of fibromodulin peptide for promoting myofibroblast differentiation and apoptosis in a subject having a disorder associated with myofibroblast activity, wherein the composition is a controlled release formulation that provides controlled release of fibromodulin peptide, and wherein the composition further comprises TGF-β1.

In some embodiments of the method, optionally in combination with any or all of the above embodiments, the medical device is a stent.

In some embodiments of the method, optionally in combination with any or all of the above embodiments, the composition further comprises a polymer, and the composition forms a coating on the medical device.

In some embodiments of the method, optionally in combination with any or all of the above embodiments, the composition comprises an effective amount of fibromodulin peptide for promoting myofibroblast differentiation and apoptosis in a subject having a disorder associated with myofibroblast activity, wherein the composition is a controlled release formulation that provides controlled release of fibromodulin peptide, and wherein the composition further comprises TGF-β1.

In some embodiments of the method, optionally in combination with any or all of the above embodiments, the device is a stent.

DETAILED DESCRIPTION OF THE INVENTION

Figure 1:
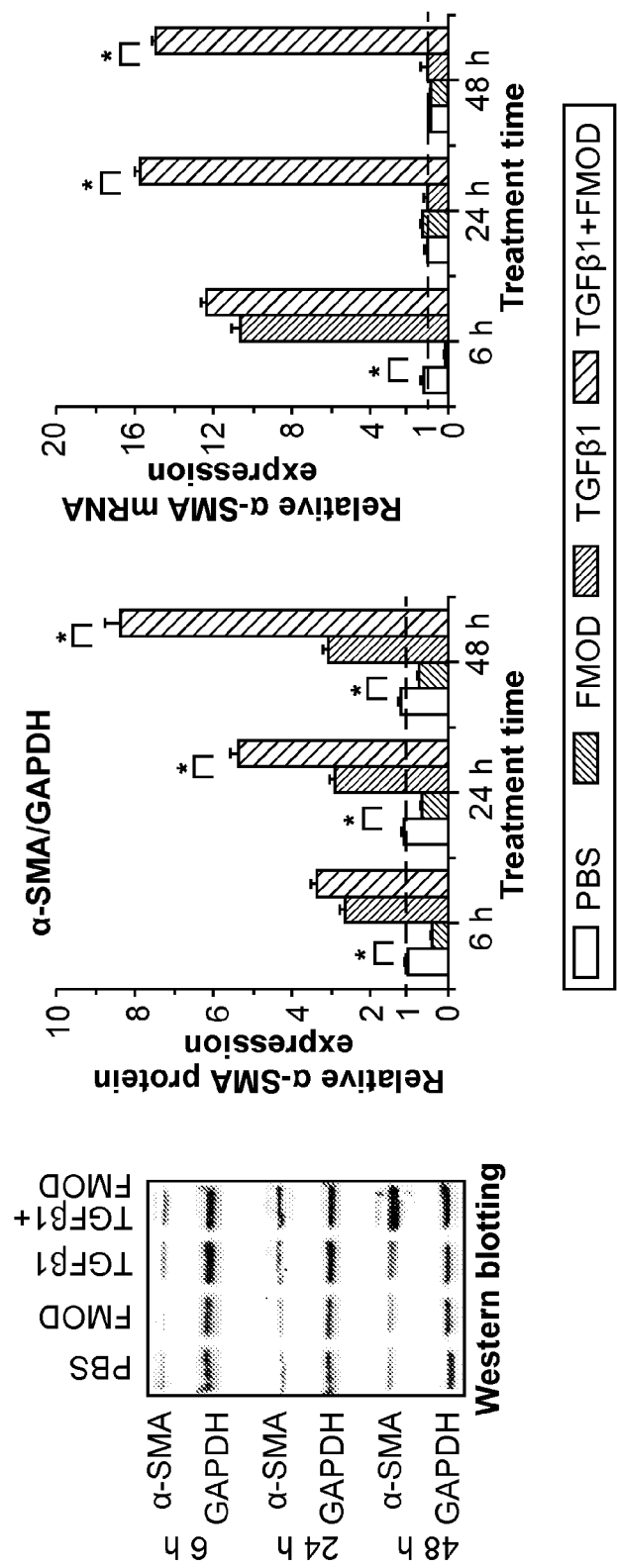
FIG. 1 summarizes results of western blotting and quantitative RT-PCR (qRT-PCR) analyses which revealed that fibromodulin (FMOD) alone had no significant effect on rat dermal fibroblast (RDF) α-smooth muscle actin (α-SMA) expression. However, when in the presence of TGF-β1, FMOD significantly enhances TGF-β1-induced α-SMA expression. Data are normalized to untreated RDFs at time 0 (dash lines). N=3. *, P<0.05.

In one aspect of the present invention, it is provided method for treating or ameliorating a disorder associated with increased or decreased myofibroblast activity, which method comprising modulating the myofibroblast level in a subject in need thereof by modulating fibromodulin level in the subject. The subject can be a mammal, e.g., a patient or an animal.

In some embodiments of the method, modulating myofibroblast level comprises increasing fibromodulin level. Increasing fibromodulin level can be achieved by endogenously increasing fibromodulin level via, e.g., genetic engineering using a DNA or cDNA sequence expressing fibromodulin protein or peptide. Genetic engineering technology is well established and can be readily achieved by a person of ordinary skill in the art.

In some embodiments, increasing fibromodulin level can be achieved by exogenously increasing fibromodulin level by, e.g., administering to a subject a fibromodulin protein or peptide. In some embodiments, such fibromodulin protein or peptide can be included in a composition, which can be formulated into various formulations for different modes of administration. More detailed description of such formulations is provided below.

In some embodiments of the method, modulating myofibroblast level comprises decreasing fibromodulin expression level. Decreasing fibromodulin expression level can be achieved by established method of decreasing expression level of a protein, e.g., gene knockout, gene deletion, etc. Such gene knockout or deletion methodologies are well established and can be readily carried out by a person of ordinary skill in the art. Decreasing fibromodulin level can decrease myofibroblast differentiation induced by a myofibroblast inducing agent and apoptosis so as to prolong myofibroblast activity.

In some embodiments of the method, modulating fibromodulin level in the subject comprises effectively modulating the level of fibromodulin activity so as to modulate activities of a myofibroblast apoptosis inducing agent. Such myofibroblast apoptosis inducing agent can be, e.g., interleukin-1β (IL-1β).

In some embodiments of the method, modulating myofibroblast level comprises applying to the subject an effective amount of fibromodulin for promoting myofibroblast differentiation and apoptosis thereby increasing the myofibroblast level in the subject where early, but short duration myofibroblast activity is effective for the disorder or inhibiting prolonged myofibroblast activity in the subject where the disorder is associated with prolonged myofibroblast activity, wherein the myofibroblast differentiation is induced by a myofibroblast inducing agent.

In some embodiments of the method, modulating myofibroblast level comprises blocking fibromodulin activity so as to prolong myofibroblast activity.

In some embodiments of the above methods, blocking fibromodulin activity comprises administering to the subject anti-sense oligonucleotides, antibodies, peptides that inhibit fibromodulin activities, and combinations thereof. Medical conditions can benefit from (e.g., treated or ameliorated) prolonged myofibroblast activity. A number of examples of such medical conditions or disorders are shown in Table 1.

In some embodiments of the above methods, modulating myofibroblast level comprises applying to the subject an effective amount of fibromodulin for promoting myofibroblast differentiation and apoptosis thereby increasing the myofibroblast level in the subject where early, but short duration myofibroblast activity is effective for the disorder or inhibiting prolonged myofibroblast activity in the subject where the disorder is associated with prolonged myofibroblast activity. Such disorders include, e.g., wounds with impaired cell motility such as diabetic wounds; wounds with impaired tensile strength such as wounds in patients on corticosteroids; wounds in olders; emphysema; interstitial lung diseases; asthma; Dupuytren's contracture.

In some embodiments of the method, the disorder is atherosclerosis, restenosis, cirrhosis, hemorrhage, microaneurysms, wounds with impaired cell motility, diabetic wounds, wounds with impaired tensile strength, wounds in patients on corticosteroids, wounds in olders, emphysema, interstitial lung diseases, asthma, Dupuytren's contracture, or another disease in Table 1.

In another aspect of the present invention, it is provided a composition. The composition comprises an effective amount of fibromodulin for promoting myofibroblast differentiation and apoptosis in a subject having a disorder associated with myofibroblast activity.

In some embodiments of the method, optionally in combination with any or all of the above embodiments, the myofibroblast differentiation inducing agent is TGF-β1.

In another aspect of the present invention, it is provided a composition, which composition comprising an effective amount of fibromodulin for promoting myofibroblast differentiation and apoptosis in a subject having a disorder associated with myofibroblast activity.

In some embodiments of the composition, the composition further comprises an excipient (e.g., a polymer or a formulation carrier described below), wherein the formulation is a formulation for topical, transdermal, intradermal, or microneedle delivery.

In some embodiments of the composition, optionally in combination with any or all the above embodiments, the composition is included in a medical device comprising the composition.

In some embodiments, the medical device is a stent.

In a further aspect of the present invention, it is provided a method of forming a medical device, comprising applying a composition of the various above embodiments to the medical device. Such applying can be, e.g., forming a coating comprising the composition on the surface of the medical device. In some embodiments, the medical device is a stent.

As used herein, the term "myofibroblast differentiation inducing agent" shall mean any proteineous or small molecule agent capable of inducing myofibroblast differentiation. An example of such myofibroblast differentiation inducing agents is transforming growth factor (TGF)-β1.

As used herein, the term "myofibroblast apoptosis inducing agent" shall mean any proteineous or small molecule agent capable of inducing myofibroblast apoptosis. An example of such myofibroblast apoptosis inducing agents is interleukin-1β (IL-1β).

As used herein, the term "increased myofibroblast activity" shall mean the level of myofibroblast activity exceeds the normal level myofibroblast activity in a subject (e.g., a human being), which is within the general knowledge of a medical practitioner. In some times, the term "increased myofibroblast activity" can be used interchangeably with the term "excessive myofibroblast activity."

As used herein, the term "decreased myofibroblast activity" shall mean the level of myofibroblast activity falls below the normal level myofibroblast activity in a subject (e.g., a human being), which is within the general knowledge of a medical practitioner. In some times, the term "decreased myofibroblast activity" can be used interchangeably with the term "insufficient myofibroblast activity."

Myofibroblast Activity and Fibromodulin

Figure 2:
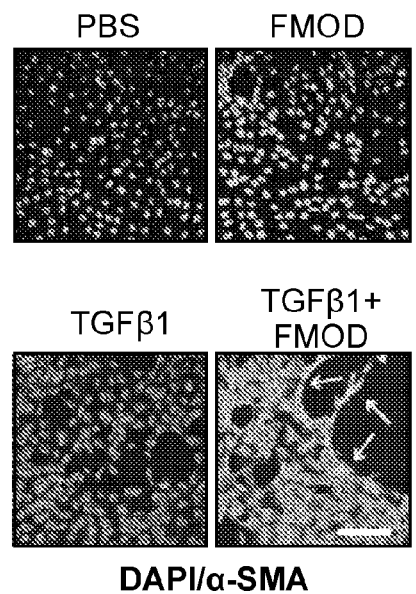
FIG. 2 shows results of an immunofluorescent (IF) staining study which revealed that FMOD, when combined with TGF-β1, significantly enhanced myofibroblast differentiation and contractility in vitro. Formation of stress fibers stained strongly for α-SMA are indicated by yellow arrows. Scale bar=100 μm.
Figure 3:
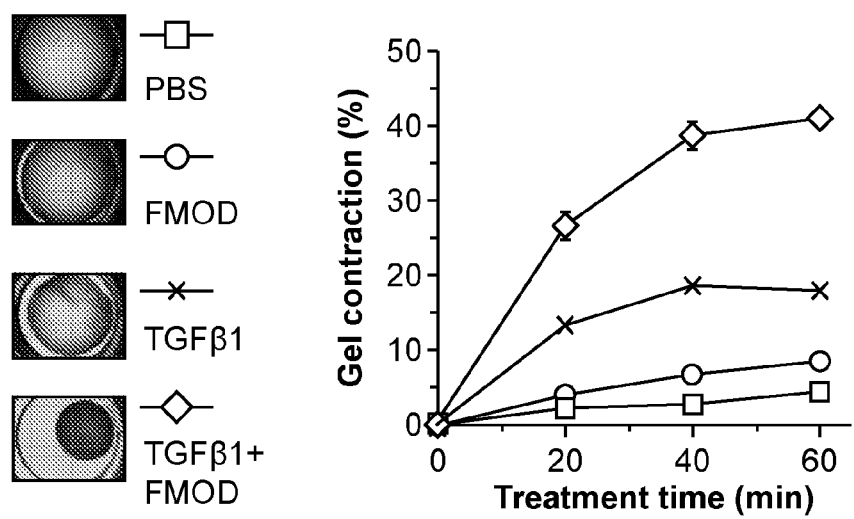
FIG. 3 shows that FMOD+TGF-β1 significantly promotes TGF-β1-mediated RDF contraction in collagen gel, while FMOD alone had minimal effects. N=6.
Figure 4:
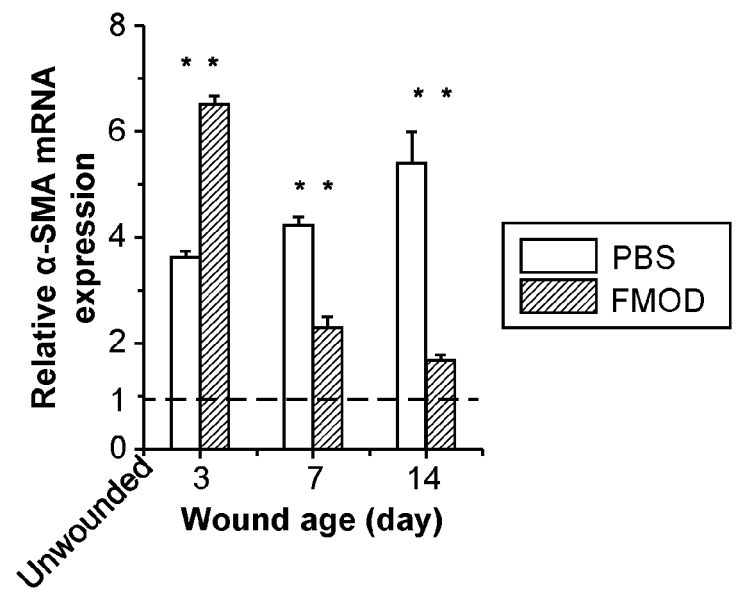
FIG. 4 shows the results of a PCR array assay which revealed that expression of α-SMA were significantly upregulated in FMOD-treated adult rat wounds at the early 3-day time-point, but reduced at the late 7- and 14-day time-points. Gene expression is normalized to unwounded skin (dashed lines). N=9 wounds from 9 animals. **, P<0.05.

Activity level of myofibroblast is related to the activity of fibromodulin. Fibromodulin can promote myofibroblast differentiation and apoptosis. Fibromodulin addition in the presence of transforming growth factor (TGF)-1β significantly promoted TGF-β1-mediated rat dermal fibroblasts (RDFs) α-smooth muscle actin (α-SMA, a wildly used myofibroblast marker) expression (FIG. 1). Remarkably, fibromodulin, when combined with TGF-β1, significantly enhanced myofibroblast differentiation and contractility in vitro (FIG. 2). Quantitative in vitro collagen gel contraction studies confirmed increased contractility of FMOD+TGF-β1 induced myofibroblasts relative to TGF-β1 alone (FIG. 3). In addition, expression of α-SMA were significantly upregulated in FMOD-treated adult rat wounds at the early 3-day time-point, but reduced at the late 7- and 14-day time-points (FIG. 4).

Figure 5:
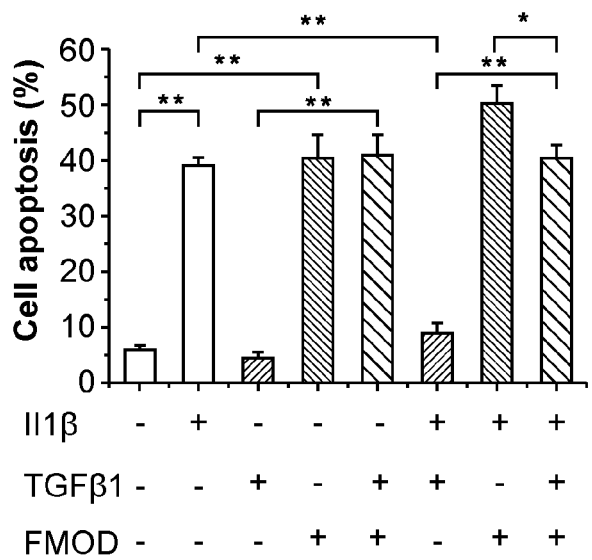
FIG. 5 shows that FMOD alone induces myofibroblast apoptosis as effectively as IL-10, even in the presence of TGF-β1. N=6. *, P<0.05; **, P<0.05.
Figure 6:
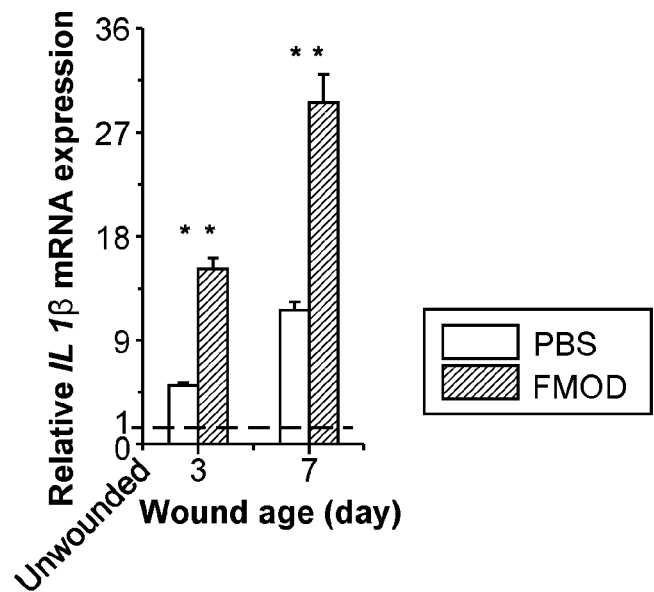
FIG. 6 shows results of PCR array assay which revealed that FMOD significantly stimulated IL-10 expression in day 3 and 7 adult rat wounds. Gene expression is normalized to unwounded skin (dashed lines). N=9 wounds from 9 animals. **, P<0.05
Figure 7:
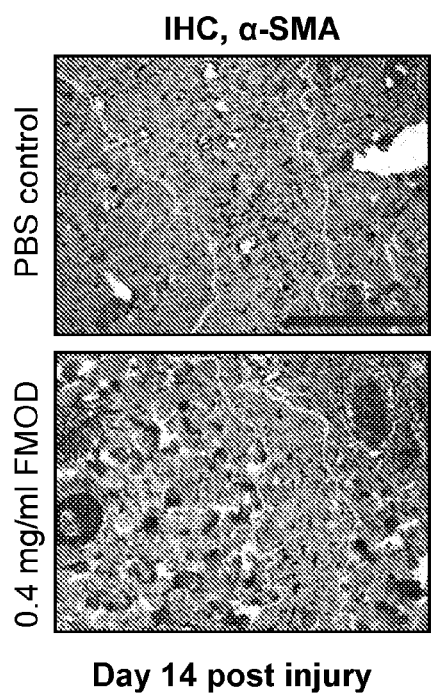
FIG. 7 shows that decreased α-SMA-positive myofibroblasts are found in FMOD-treated wounds at day 14 post injury. Scale bar=200 μm.

Notably, TGF-β1 completely blocked interleukin (IL)-β1-mediated apoptosis in myofibroblasts (FIG. 5). Surprisingly, FMOD alone promoted myofibroblast apoptosis as effectively as IL-1β, but more strikingly, FMOD administration promoted apoptosis even in the presence of TGF-1β (FIG. 5). Furthermore, FMOD significantly stimulated IL-1β expression in day 3 and 7 adult rat wounds (FIG. 6), which correlated functionally with diminished α-SMA-positive myofibroblast numbers by day 14 post injury (FIG. 7). Taken together, FMOD not only promotes TGF-β1-induced myofibroblast differentiation and contractility, but also accelerates myofibroblast clearance—resulting in lack of myofibroblast persistence in remodeling stage of FMOD-treated wounds.

As used herein, the term "fibromodulin" includes fibromodulin protein and peptides. Examples of fibromodulin protein and peptides are described in U.S. patent application Ser. No. 13/322,124, which is a national phase application of PCT/US2010/036262. Teachings in these applications are incorporated herein in their entirety by reference. An example of FMOD (SEQ ID NO:1; Genebank NM 002023) refers to a fibromodulin molecule as generally known in the art. Other examples of FMOD molecules are disclosed in (Heinegard, Larsson et al. 1986), as shown in SEQ ID NO:1, and SEQ ID NO:2 (Genebank BC035381), SEQ ID NO:3 (Genebank U05291), SEQ ID NO:4 (Genebank AK303866), SEQ ID NO:5 (Genebank AK172740), SEQ ID NO:6 (Genebank AK092999), SEQ ID NO:7 (Genebank AK027694), SEQ ID NO:8 (Genebank DQ892112), SEQ ID NO:9 (Genebank X72913), SEQ ID NO:10 (Genebank S75546), SEQ ID NO:11 (Genebank AY890642), SEQ ID NO:12 (Genebank AY893119). Information for these sequences is:

```
SEQ ID NO: 1: NH2-
WTSLLLLAGLFSLSQAQYEDDPHWWFHYLRSQQSTYYDPYDPYPYETYEP

YPYGVDEGPAYTYGSPSPPDPRDCPQECDCPPNFPTAMYCDNRNLKYLPF

VPSRMKYVYFQNNQITSIQEGVFDNATGLLWIALHGNQITSDKVGRKVFS

KLRHLERLYLDHNNLTRMPGPLPRSLRELHLDHNQISRVPNNALEGLENL

TALYLQHNEIQEVGSSMRGLRSLILLDLSYNHLRKVPDGLPSALEQLYME

HNNVYTVPDSYFRGAPKLLYVRLSHNSLTNNGLASNTFNSSSLLELDLSY

NQLQKIPPVNTNLENLYLQGNRINEFSISSFCTVVDVVNFSKLQVLRLDG

NEIKRSAMPADAPLCLRLASLIEI-COOH

SEQ ID NO: 2: NH2-
MQWTSLLLLAGLFSLSQAQYEDDPHWWFHYLRSQQSTYYDPYDPYPYET

YEPYPYGVDEGPAYTYGSPSPPDPRDCPQECDCPPNFPTAMYCDNRNLKY
```

LPFVPSRMKYVYFQNNQITSIQEGVFDNATGLLWIALHGNQ

ITSDKVGRKVFSKLRHLERLYLDHNNLTRMPGPLPRSLRELHLDHNQISR

VPNNALEGLENLTALYLQHNEIQEVGSSMRGLRSLILLDLSYNHLRKVPD

GLPSALEQLYMEHNNVYTVPDSYFRGAPKLLYVRLSHNSLTNNGLASNTF

NSSSLLELDLSYNQLQKIPPVNTNLENLYLQGNRINEFSISSFCTVVDVV

NFSKLQVLRLDGNEIKRSAMPADAPLCLRLASLIEI-COOH

SEQ ID NO: 3: NH$_2$-
YLQGNRINEFSISSFCTVVDVVNFSKLQVLRLDGNEIKRSAMPADAPLCL

RLASLIEI-COOH

SEQ ID NO: 4: NH$_2$-
QWTSLLLLAGLFSLSQAQYEDDPHWWFHYLRSQQSTYYDPYDPYPYETY

EPYPYGVDEGPAYTGSPSPPDPRDCPQECDCPPNFPFVPSRMKYVYFQN

NQITSIQEGVFDNATGLLWIALHGNQITSDKVGRKVFSKLRHLERLYLDH

NNLTRMPGPLPRSLRELHLDHNQISRVPNNALEGLENLTALYLQHNEIQE

VGSSMRGLRSLILLDLSYNHLRKVPDGLPSALEQLYMEHNNVYTVPDSYF

RGAPKLLYVRLSHNSLTNNGLASNTFNSSSLLELDLSYNQLQKIPPVNT

NLENLYLQGNRINEFSISSFCTVVDVVNFSKLQVLRLDGNEIKRSAMPAD

APLCLRLASLIEI-COOH

SEQ ID NO: 5: NH$_2$-
MKMTLIGGSTTSAASSPPTTIPMTLTRMRPTSLTPMGWMKGQPTPTALHL

DHNQISRVPNNALEGLENLTAMYCDNRNLKYLPFVPSRMKYVYFQNNQIT

SIQEGVFDNATGLLWIALHGNQITSDKVGRKVFSKLRHLERLYLDHNNLT

RMPGPLPRSLRELHLDHNQIPATAPRNATAHPTSRPCTSNTMRSRKWAV

P-COOH

SEQ ID NO: 6: NH$_2$-
MKMTLIGGSTTSAASSPPTTIPMTLTRMRPTSLTPMGWMKGQPTPTALHP

LQIPATAPRKVFSKLRHLERLYLDHNNLTRMPGPLPRSLRELHLDHNQIS

RVPNNALEGLENLTALYLQHNEIQEVGSSMRGLRSLILLDLSYNHLRKVP

DGLPSALEQLYMEHNNVYTVPDSYFRGAPKLLYVRLSHNSLTNNGLASNT

FNSSSLLELDLSYNQLQKIPPVNTNLENLYLQGNRINEFSISSFCTVVDV

VNFSKLQVLRLDGNEIKRSAMPADAP LCLRLASLIEI-COOHSEQ

SEQ ID NO: 7: NH$_2$-
MQWTSLLLLAGLFSLSQAQYEDDPHWWFHYLRSQQSTYYDPYDPYPYET

YEPYPYGVDEGPAYTGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIEI-COOH

SEQ ID NO: 8: NH$_2$-
MQWTSLLLLAGLFSLSQAQYEDDPHWWFHYLRSQQSTYYDPYDPYPYET

YEPYPYGVDEGPAYTGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIEI-COOH

SEQ ID NO: 9: NH$_2$-
MQWTSLLLLAGLFSLSQAQYEDDPHWWFHYLRSQQSTYYDPYDPYPYET

YEPYPYGVDEGPAYTGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLYLLDLSYNHLRKVPDGLPSALEQL

YMEHINNVYTVPDSYFRGAPKLLYVRLSHNSLTNNGLASNTFNSSSLLEL

DLSYNQLQKIPPVNTNLENLYLQGNRINEFSISSFCTVVDVVNFSQLQVV

RLDGNEMKRSAMPAEAPLCLRLASLIEI-COOH

SEQ ID NO: 10: NH$_2$-
MQWASLLLLAGLFSLSQAQYEDDPHWWFHYLRSQQSTYYDPYDPYPYET

YEPYPYGVDEGPAYTGSPSPPDPRDCPQECDCPPNFLTAMYCDNRNLKY

PFVPSRMKYVYFQNNQITSIQEGVFDNATGLLWIALHGNQITSDKVGRKV

FSKLRHLERLYLDHNNLTRMPGPLPRSLRELHLDHNQISRVPNNALEGLE

NLTALYLQHDEIQEVGSSMRGLRSLILLDLSYNHLRKVPDGLPSALEQLY

MEHNNVYTVPDSYFRGAPKLLYVRLSHNSLTNNGLASNTFNSSSLELDLS

YNQLQKIPPVNTNLENLYLQGNRINEFSISSFCTVVDVVNFSKLQVVRLD

GNEIKRSAMPADAPLCLRLASLIEI-COOH

SEQ ID NO: 11: NH$_2$-
MQWTSLLLLAGLFSLSQAQYEDDPHWWFHYLRSQQSTYYDPYDPYPYET

YEPYPYGVDEGPAYTGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIGI-COOH

SEQ ID NO: 12: NH$_2$-
MQWTSLLLLAGLFSLSQAQYEDDPHWWFHYLRSQQSTYYDPYDPYPYET

YEPYPYGVDEGPAYTGSPSPPDPRDCPQECDCPPNFPTAMYCDNRNLKY

LPFVPSRMKYVYFQNNQITSIQEGVFDNATGLLWIALHGNQITSDKVGRK

VFSKLRHLERLYLDHNNLTRMPGPLPRSLRELHLDHNQISRVPNNALEGL

ENLTALYLQHNEIQEVGSSMRGLRSLILLDLSYNHLRKVPDGLPSALEQL

YMEHNNVYTVPDSYFRGAPKLLYVRLSHNSLTNNGLASNTFNSSSLLELD

LSYNQLQKIPPVNTNLENLYLQGNRINEFSISSFCTVVDVVNFSKLQVLR

LDGNEIKRSAMPADAPLCLRLASLIEIL-COOH

As used herein, the term TGF-β isoform refers to a TGF-β peptide having a shorter amino acid sequence as compared to TGF-β that retains the function and binding sites of TGF-β. In some embodiments, the term TGF-β isoform can be used interchangeably with the term TGF-β peptide. Examples of such TGF-β isoforms are TGF-β-1 (SEQ ID NO:64), TGF-β-2 (SEQ ID NO:65), and TGF-β-3 (SEQ ID NO:66). Information for these sequences is:

SEQ ID NO: 64: NH$_2$-
ALDTNYCFSSTEKNCCVRQLYIDFRKDLGWKWIHEPKGYHANFCLGPCPY

IWSLDTQYSKVLALYNQHNPGASAAPCCVPQALEPLPIVYYVGRKPKVEQ

LSNMIVRSCKCS-COOH

SEQ ID NO: 65: NH$_2$-
QDNCCLRPLYIDFKRDLGWKWIHEPKGYNANFCAGACPYLWSSDTQHRV

LSLYNTINPEASASPCCVSQDLEPLTI LYYIGKTPKIEQLSNMIVKSCK

CS-COOH

SEQ ID NO: 66: NH$_2$-
NCCVRPLYIDFRQDLGWKWVHEPKGYYANFCSGPCPYLRSA

DTTHSTVLGLYNTLNPEASASPCCVPQDLEPLTILYYVGRTPKVEQLSNM

VVKSCKCS-COOH

As used herein, the term "beneficial effect" refers to a biologically significant improvement of a body condition, which is readily ascertainable by a person of ordinary or specialized skill in the art, depending on the "beneficial effect" described. For instance, if the "beneficial effect" is improvement in scar appearance, then a person of ordinary skill can make that ascertainment. However, if the "beneficial effect" is decreased biliary stent stenosis or decreased coronary vessel stent stenosis or decreased intra-abdominal adhesions, then a person of specialized skill is required to make that ascertainment.

Fibromodulin Peptides

As used herein, the term fibromodulin peptide (FMOD-P) refers to a FMOD isoform having a shorter amino acid sequence as compared to FMOD that retains some of the function and binding sites of fibromodulin (FMOD) or perhaps novel function and binding sites not normally exposed in FMOD. In some embodiments, FMOD-P can be used interchangeably with the term FMOD isoform. Throughout the whole document of the instant application, FMOD-P is sometimes described as FMOD peptide(s), invention FMOD-P(s) or invention FMOD peptide(s).

In some embodiments, the term FMOD-P encompasses a functional or structural derivative of the invention FMOD-P. Such derivatives can be made by, e.g., derivatizing an invention FMOD-P by established methodology, e.g., chemical modification or physical modification. Chemical modification includes, e.g., modification using an acid, a base, esterification, PEGylation, or alkylation with a short chain alkyl group. Physical modification includes, e.g., heating, moisture treatment, light treatment, mechanical impact, etc.

Examples of FMOD-P include, but are not limited to, peptides of the following sequences: SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, and SEQ ID NO:63.

Sequence information for some of the amino acid sequences is listed as follows:

SEQ ID NO: 13: NH$_2$-
NRNLKYLKPFVPSRMK-COOH

SEQ ID NO: 14: NH$_2$-
FQNNQITSIQEGVFDNATGLL-COOH

SEQ ID NO: 15: NH$_2$-
NRNLKYLKPFVPSRMK-COOH

SEQ ID NO: 16: NH$_2$-
YLRSQQSTYYDPYDPYPYETYEPYPYGVDEGPAYTY

GSPSPPDPRDCPQECDCPPNFPTAMYCD-COOH

SEQ ID NO: 17: NH$_2$-
PYGVDEGPAYTYGSPSPPDPRDCPQECDCPPNFPTAMYCD-COOH

SEQ ID NO: 18: NH$_2$-
SRMKYVYFQNNQITSIQEGVFDNATGLLWIALHGNQITS-COOH

SEQ ID NO: 19: NH$_2$-
NRNLKYLPFVPSRMKYVYFQNNQITSIQEGVFDNATGLLWIAL

HGNQITS-COOH

SEQ ID NO: 20: NH$_2$-
DKVGRKVFSKLRHLERLYLDHNNLTRMPGPLPRSLRELHLDHNQI-

COOH

SEQ ID NO: 21: NH$_2$-
SRVPNNALEGLENLTALYLQHNEIQEVGSSMRGLRSLILLDLSYNHLRKV

PDGLPSALEQLYMEHNNV-COOH

SEQ ID NO: 22: NH$_2$-
YTVPDSYFRGAPKLLYVRLSHNSLTNNGLASNTFNSSSLLELDLSYNQLQ

KIPPVNTNLENLYLQGNRI-COOH

SEQ ID NO: 23: NH$_2$-
NEFSISSFCTVVDVVNFSKLQVLRLDGNEIKRSAMPADAPLCLRLASLIE

I-COOH

SEQ ID NO: 24: NH$_2$-
QWTSLLLLAGLFSLSQAQYEDDPHWWFHYLRSQQSTYYDP-COOH

SEQ ID NO: 25: NH$_2$-
DDPHWWFHYLRSQQSTYYDPYDPYPYETYEPYPYGVDEGP-COOH

SEQ ID NO: 26: NH$_2$-
DPRDCPQECDCPPNFPTAMYCDNRNLKYLPFVPSRMKYVYFQNNQITSI

Q-COOH

SEQ ID NO: 27: NH$_2$-
YGSPSPPDPRDCPQECDCPPNFPTAMYCDNRNLKYLPFVPSRMKYVYFQN

N-COOH

SEQ ID NO: 28: NH$_2$-
FPTAMYCDNRNLKYLPFVPSRMKYVYFQNNQITSIQEGVFDNATGLLWI

A-COOH

-continued

SEQ ID NO: 29: NH₂-
LLWIALHGNQITSDKVGRKVFSKLRHLERLYLDHNNLTRMPGPLPRSLRE
LHLDHNQI-COOH

SEQ ID NO: 30: NH₂-
AYTYGSPSPPDPRDCPQECDCPPNFPTAMYCDNRNLKYLPFVPSRMKYV
Y-COOH

SEQ ID NO: 31: NH₂-
SRVPNNALEGLENLTALYLQHNEIQEVGSSMRGLRSLILLDLSYNHL-
COOH

SEQ ID NO: 32: NH₂-
RKVPDGLPSALEQLYMEHNNVYTVPDSYFRGAPKLLYVRLSHNSLT-
COOH

SEQ ID NO: 33: NH₂-
NNGLASNTFNSSSLLELDLSYNQLQKIPPVNTNLENLYLQGNRI-COOH

SEQ ID NO: 34: NH₂-
TSIQEGVFDNATGLLWIALHGNQITSDKVGRKVFSKLRHLERLYLDHNN
L-COOH

SEQ ID NO: 35: NH₂-
TRMPGPLPRSLRELHLDHNQISRVPNNALEGLENLTALYLQHNEIQE-
COOH

SEQ ID NO: 36: NH₂-
VGSSMRGLRSLILLDLSYNHLRKVPDGLPSALEQLYMEHNNV-COOH

SEQ ID NO: 37: NH₂-
YTVPDSYFRGAPKLLYVRLSHNSLTNNGLASNTFNSSSLLELDLSYNQL-
COOH

SEQ ID NO: 38: NH₂-
QKIPPVNTNLENLYLQGNRINEFSISSFCTVVDVVNFSKLQVLRLDGNE
I-COOH

SEQ ID NO: 39: NH₂-
DKVGRKVFSKLRHLERLYLDHNNLTRMPGPLPRSLRELHLDHNQISRVPN
NALEGLEN-COOH

SEQ ID NO: 40: NH₂-
NATGLLWIALHGNQITSDKVGRKVFSKLRHLERLYLDHNN-COOH

SEQ ID NO: 41: NH₂-
NATGLLWIALHGNQITSDKVGRKVFSKLRHLERLYLDHNNLTRMPGPLPR
SLRELHLDHNQISRVPNNALEGLEN-COOH

SEQ ID NO: 42: NH₂-
NLTALYLQHNEIQEVGSSMRGLRSLILLDLSYNHLRKVPDGLPSALEQLY
MEHNNVYTVPDSYFRGAPKLLYVRLSHNSLTNNGLASNTFN-COOH

SEQ ID NO: 43: NH₂-
TRMPGPLPRSLRELHLDHNQISRVPNNALEGLENLTALYLQHNEIQEVGS
SMRGLRSLILLDLSYNHL-COOH

SEQ ID NO: 44: NH₂-
RKVPDGLPSALEQLYMEHNNVYTVPDSYFRGAPKLLYVRLSHNSLTNNG
LASNTFN-COOH

SEQ ID NO: 45: NH₂-
NSSSLLELDLSYNQLQKIPPVNTNLENLYLQGNRINEFSISSFC-COOH

SEQ ID NO: 46: NH₂-
CTVVDVVNFSKLQVLRLDGNEIKRSAMPADAPLC-COOH

SEQ ID NO: 47: NH₂-
QKIPPVNTNLENLYLQGNRINEFSISSFCTVVDVVNFSKLQVLRLDGNEI
KRSAMPADAPLC-COOH

SEQ ID NO: 48: NH₂-
CPQECDCPPNFPTAMYCDNRNLKYLPFVPSRMKYVYFQNNQI-COOH

SEQ ID NO: 49: NH₂-
ATGLLWIALHGNQITSDKVGRKVFSKLRHLERLYLDHNNLTRMPGPLPRS
LRELHLDHNQIS-COOH

SEQ ID NO: 50: NH₂-
NLTRMPGPLPRSLRELHLDHNQISRVPNNALEGLENLTALYLQHNEIQE-
COOH

SEQ ID NO: 51: NH₂-
NLTRMPGPLPRSLRELHLDHNQISRVPNNALEGLEN-COOH

SEQ ID NO: 52: NH₂-
GLPSALEQLYMEHNNVYTVPDSYFRGAPKLLYVRLSHNSLTNNGLAS-
COOH

SEQ ID NO: 53: NH₂-
HLDHNQISRVPNNALEGLENLTALYLQHNEIQEVGSSMRG-COOH

SEQ ID NO: 54: NH₂-
FSKLQVLRLDGNEIKRSAMPADAPLCRLASLIE-COOH

SEQ ID NO: 55: NH₂-
PNNALEGLENLTALYLQHNEIQEVGSSMRGLRSLILLDL-COOH

SEQ ID NO: 56: NH₂-
PDGLPSALEQLYMEHNNVYTVPDSYFRGAPKLLYVRLSHNSLTNNGLAS-
COOH

SEQ ID NO: 57: NH₂-
LLDLSYNHLRKVPDGLPSALEQLYMEHNNVYTVPDSYFRG-COOH

SEQ ID NO: 58: NH₂-
SKLRHLERLYLDHNNLTRMPGPLPRSLRELHLDHNQISRVPNNALEGLE
N-COOH

SEQ ID NO: 59: NH₂-
LRSLILLDLSYNHLRKVPDGLPSALEQLYMEHNNVYTVPD-COOH

SEQ ID NO: 60: NH₂-
YVRLSHNSLTNNGLASNTFNSSSLLELDLSYNQLQKIPPV-COOH

SEQ ID NO: 61: NH₂-
NNGLASNTFNSSSLLELDLSYNQLQKIPPVNTNLENLYLQ-COOH

SEQ ID NO: 62: NH₂-
HWWFHYLRSQQSTYYDPYDPYPYETYEPYPYGVDEGPAYTGSPSPPDPR
D-COOH

SEQ ID NO: 63: NH₂-
HNSLTNNGLASNTFNSSSLLELDLSYNQLQKIPPVNTNL-COOH

The FMOD-P disclosed herein can be made by a method comprising: designing a peptide having a shorter amino acid sequence as compared to FMOD that retains the function and binding sites of FMOD or perhaps novel function and binding sites not normally exposed in FMOD; and preparing the peptide.

In some embodiments, the act of designing can include steps of performing a hydrophobic analysis of a primary or secondary structure of FMOD and finding the binding site of FMOD.

In some embodiments, the act of preparing comprises splicing a FMOD at a specific site or sites so as to form a peptide as defined. Splicing a protein to form a peptide at a site or sites are well established laboratory techniques, which can be readily performed by a person of ordinary skill in the art.

In some further embodiments, the act preparing the peptide includes expressing the peptide in a recombinant system or producing the peptide in a cell free system (e.g., a cell free translation system). Such a recombinant system can be a bacteria, yeast, mammalian cell, or plant cell, which can be readily performed by a person of ordinary skill in the art.

In some other embodiments, preparing comprises synthesizing the FMOD-P using peptide synthesizer machines.

Formulation Carrier

The composition described herein may be administered to a subject in need of treatment by a variety of routes of administration, including orally and parenterally, (e.g., intravenously, subcutaneously or intramedullary), intranasally, as a suppository or using a "flash" formulation, i.e., allowing the medication to dissolve in the mouth without the need to use water, topically, intradermally, subcutaneously and/or administration via mucosal routes in liquid or solid form. The pharmaceutical composition can be formulated into a variety of dosage forms, e.g., extract, pills, tablets, microparticles, capsules, oral liquid.

There may also be included as part of the composition pharmaceutically compatible binding agents, and/or adjuvant materials. The active materials can also be mixed with other active materials including antibiotics, antifungals, other virucidals and immunostimulants which do not impair the desired action and/or supplement the desired action.

In some embodiments, the composition can be formulated into a formulation for bone, which can include a carrier such as collagen, atelocollagen (collagen treated to remove the immunogenic ends), hydroxyapatite, and a polymer, which is further described below. In these embodiments, the formulation can comprise a porous matrix or microspheres made of a polymeric material, which is further described below. In some embodiments, the polymer can be, e.g., polylactic acid or polylactide (PLA), or poly(lactic acid-co-glycolic acid), or another bioabsorbable polymer.

In one embodiment, the mode of administration of the pharmaceutical composition described herein is oral. Oral compositions generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. Some variation in dosage will necessarily occur, however, depending on the condition of the subject being treated. These preparations should produce a serum concentration of active ingredient of from about 0.01 nM to 1,000,000 nM, e.g., from about 0.2 to 40 µM. A preferred concentration range is from 0.2 to 20 µM and most preferably about 1 to 10 µM. However, the concentration of active ingredient in the drug composition itself depends on bioavailability of the drug and other factors known to those of skill in the art.

In another embodiment, the mode of administration of the pharmaceutical compositions described herein is topical or mucosal administration. A specifically preferred mode of mucosal administration is administration via female genital tract. Another preferred mode of mucosal administration is rectal administration.

Various polymeric and/or non-polymeric materials can be used as adjuvants for enhancing mucoadhesiveness of the pharmaceutical composition disclosed herein. The polymeric material suitable as adjuvants can be natural or synthetic polymers. Representative natural polymers include, for example, starch, chitosan, collagen, sugar, gelatin, pectin, alginate, karya gum, methylcellulose, carboxymethylcellulose, methylethylcellulose, and hydroxypropylcellulose. Representative synthetic polymers include, for example, poly(acrylic acid), tragacanth, poly(methyl vinylether-co-maleic anhydride), poly(ethylene oxide), carbopol, poly(vinyl pyrrolidine), poly(ethylene glycol), poly(vinyl alcohol), poly(hydroxyethylmethylacrylate), and polycarbophil. Other bioadhesive materials available in the art of drug formulation can also be used (see, for example, Bioadhesion—Possibilities and Future Trends, Gurny and Junginger, eds., 1990).

It is to be noted that dosage values also vary with the specific severity of the disease condition to be alleviated. It is to be further understood that for any particular subject, specific dosage regimens should be adjusted to the individual need and the professional judgment of the person administering or supervising the administration of the aforesaid compositions. It is to be further understood that the concentration ranges set forth herein are exemplary only and they do not limit the scope or practice of the invention. The active ingredient may be administered at once, or may be divided into a number of smaller doses to be administered at varying intervals of time.

The composition may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. Materials used in preparing these various compositions should be pharmaceutically pure and non-toxic in the amounts used.

The solutions or suspensions may also include the following components: a sterile diluent such as water for injection, saline solution, fixed oils, polyethylene glycols, glycerin, propylene glycol or other synthetic solvents; antibacterial agents such as benzyl alcohol or methylparabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The composition of the present invention can be prepared as formulations with pharmaceutically acceptable carriers. Preferred are those carriers that will protect the active compound against rapid elimination from the body, such as a controlled release formulation, including implants and microencapsulated delivery systems. Biodegradable, biocompatible polymers can be used, such as polyanhydrides, polyglycolic acid, collagen, and polylactic acid. Methods for preparation of such formulations can be readily performed by one skilled in the art.

Liposomal suspensions (including liposomes targeted to infected cells with monoclonal antibodies to viral antigens) are also preferred as pharmaceutically acceptable carriers. Methods for encapsulation or incorporation of compounds into liposomes are described by Cozzani, I.; Joni, G.; Bertoloni, G.; Milanesi, C.; Sicuro, T. Chem. Biol. Interact. 53, 131-143 (1985) and by Joni, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15(1), 67-70 (1987) and Joni, G.; Reddi, E.; Cozzani, I.; Tomio, L. Br. J. Cancer, 53(5), 615-21 (1986).

The composition described herein may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like according to a specific dosage form.

Thus, for example, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

The composition described herein can be formulated alone or together with the other agent in a single dosage form or in a separate dosage form. Methods of preparing various pharmaceutical formulations with a certain amount of active ingredient are known, or will be apparent in light of this disclosure, to those skilled in this art. For examples of methods of preparing pharmaceutical formulations, see Remington's Pharmaceutical Sciences, Mack Publishing Company, Easton, Pa., 19th Edition (1995).

In some embodiments, the composition of the various embodiments disclosed above can be formulated into implants, scaffolds, patches, etc.

EXAMPLES

The embodiments of the present invention will be illustrated by the following set forth examples. All parameters and data are not to be construed to unduly limit the scope of the embodiments of the invention.

Example 1

Using fibromodulin protein and peptide to accelerate myofibroblast differentiation and apoptosis or to inhibit prolonged myofibroblast activity has been tested, and the results are positive (data not shown).

Figure 8A:
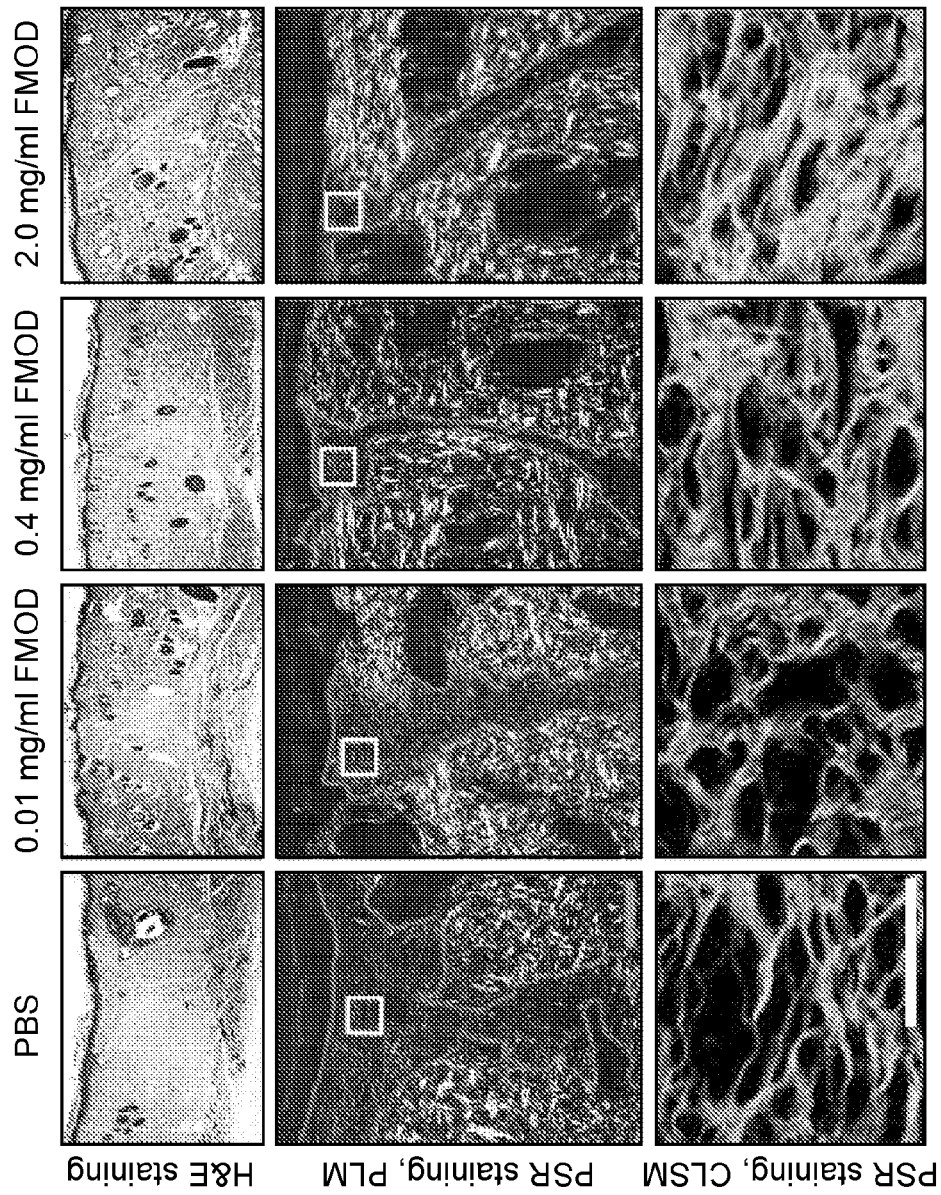
FIGS. 8A-8C show that FMOD reduces scar formation in adult rat wounds and increases tensile strength. At doses □ 0.4 mg/ml, histological (A) and quantitative analyses (B) demonstrate that FMOD significantly reduces scar size of adult rat skin wounds compared to control at day 14 post injury, while increasing tensile strength in a dose dependent manner (C). Scale bar=25 μm.
Figure 8C:
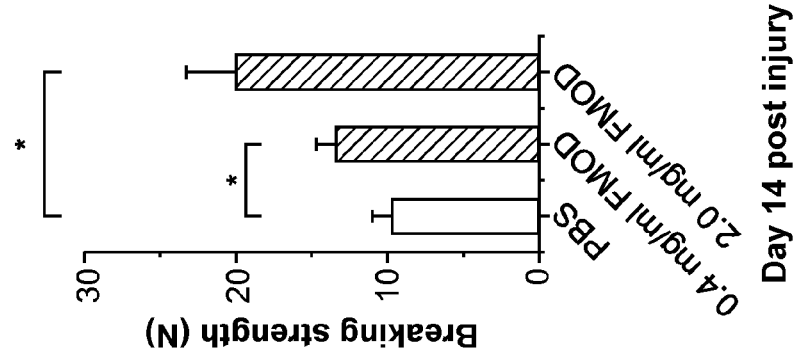
Figure 8B:
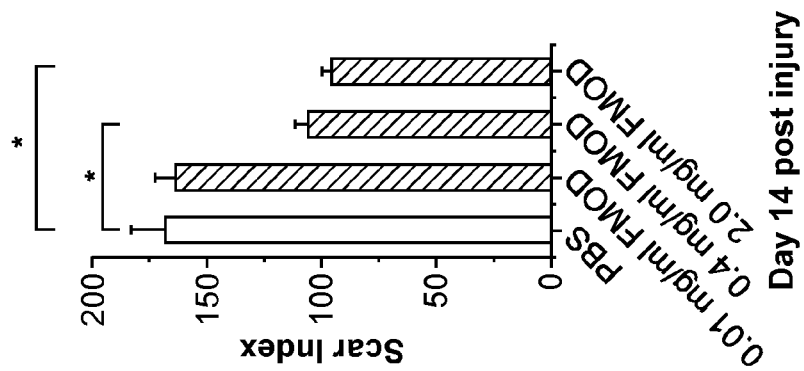

Expression of α-SMA were significantly upregulated in FMOD-treated adult rat wounds at the early 3-day time-point, but reduced at the late 7- and 14-day time-point (FIG. 4). Notably, TGF-β1 completely blocked interleukin (IL)-1β-mediated apoptosis in myofibroblasts (FIG. 5). Surprisingly, FMOD alone promoted myofibroblast apoptosis as effectively as IL-1β, but more strikingly, FMOD administration promoted apoptosis even in the presence of TGF-1β (FIG. 5). Furthermore, FMOD significantly stimulated IL-1β expression in day 3 and 7 adult rat wounds (FIG. 6), which correlated functionally with diminished α-SMA-positive myofibroblast numbers by day 14 post injury (FIG. 7). Taken together, FMOD not only promotes TGF-β1-induced myofibroblast differentiation and contractility, but also accelerates myofibroblast clearance—resulting in lack of myofibroblast persistence in remodeling stage of FMOD-treated wounds. As the result of this, FMOD treated adult rat primary closure wounds healed with significant smaller scar accompanied with more organized collagen architecture and stronger tensile strength (FIG. 8).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A composition without water, comprising an effective amount of fibromodulin peptide for promoting myofibroblast differentiation and apoptosis in a subject having a disorder associated with myofibroblast activity,
   wherein the composition is in a controlled release formulation that provides controlled release of fibromodulin peptide, and
   wherein the controlled release formulation comprises microparticles, thereby providing the effective amount of fibromodulin peptide for promoting myofibroblast differentiation and apoptosis, the effective amount of fibromodulin peptide being in a concentration of 0.01 mg/mL or from 0.4 mg/mL to 2.0 mg/mL.

2. The composition of claim 1, further comprising an excipient, wherein the formulation is a formulation for topical, transdermal, intradermal, or microneedle delivery.

3. The composition of claim 2, wherein the excipient comprises a polymer.

4. The composition of claim 1, formulated in a dosage form selected from an extract, pills, tablets, capsules, oral liquid.

5. The composition of claim 1, further comprising an agent selected from the group consisting of antibiotics, antifungals, virucidals and immunostimulants.

6. The composition of claim 1, wherein the effective amount is effective for bone formation.

7. The composition of claim 2, wherein the excipient is a carrier selected from collagen, atelocollagen, hydroxyapatite, and a polymer.

8. The composition of claim 7, wherein the polymer is a bioabsorbable polymer.

9. The composition of claim 7, wherein the polymer is polylactide (PLA), or poly (lactic acid-co-glycolic acid).

10. A method of forming a medical device, comprising forming a composition without water, the composition comprising an effective amount of fibromodulin peptide in a controlled release formulation that provides a controlled release of the fibromodulin peptide, and applying the composition to the medical device, the composition is effective for promoting myofibroblast differentiation and apoptosis in a subject having a disorder associated with myofibroblast activity,
wherein the controlled release formulation comprises microparticles, thereby providing the effective amount of fibromodulin peptide for promoting myofibroblast differentiation and apoptosis, the effective amount of fibromodulin peptide being in a concentration of 0.01 mg/mL or from 0.4 mg/mL to 2.0 mg/mL.

11. The method of claim 10, wherein the medical device is a stent.

12. The method of claim 10, wherein the composition further comprises a polymer, and wherein the composition forms a coating on the medical device.

13. A medical device comprising a composition without water, the composition comprising an effective amount of fibromodulin peptide for promoting myofibroblast differentiation and apoptosis in a subject having a disorder associated with myofibroblast activity,
wherein the composition is a controlled release formulation that provides controlled release of fibromodulin peptide, and
wherein the controlled release formulation comprises microparticles, thereby providing the effective amount of fibromodulin peptide for promoting myofibroblast differentiation and apoptosis, the effective amount of fibromodulin peptide being in a concentration of 0.01 mg/mL or from 0.4 mg/mL to 2.0 mg/mL.

14. The medical device of claim 13, which is a stent.

* * * * *